US010407733B2

(12) United States Patent
Ng

(10) Patent No.: US 10,407,733 B2
(45) Date of Patent: Sep. 10, 2019

(54) METHODS AND DEVICES FOR NASOPHARYNGEAL CARCINOMA SCREENING

(71) Applicant: Advance Sentry Corporation, Markham (CA)

(72) Inventor: Raymond Hin Wai Ng, Markham (CA)

(73) Assignee: ADVANCE SENTRY CORPORATION, Markham, Ontario ( * ) Notice: Subject to any disclaimer, the term of this patent is extended or adjusted under 35 U.S.C. 154(b) by 556 days.

(21) Appl. No.: 15/026,623

(22) PCT Filed: Oct. 3, 2014

(86) PCT No.: PCT/CA2014/000722
§ 371 (c)(1),
(2) Date: Apr. 1, 2016

(87) PCT Pub. No.: WO2015/048883
PCT Pub. Date: Apr. 9, 2015

(65) Prior Publication Data
US 2016/0251724 A1 Sep. 1, 2016

Related U.S. Application Data

(60) Provisional application No. 61/886,807, filed on Oct. 4, 2013.

(51) Int. Cl.
*C12Q 1/68* (2018.01)
*C12Q 1/6886* (2018.01)
(Continued)

(52) U.S. Cl.
CPC ............ *C12Q 1/6886* (2013.01); *A61B 10/02* (2013.01); *C12Q 1/705* (2013.01);
(Continued)

(58) Field of Classification Search
None
See application file for complete search history.

(56) References Cited

U.S. PATENT DOCUMENTS 6,494,845 B2   12/2002   Rutenberg
7,004,913 B1    2/2006   Rutenberg et al.
(Continued)

FOREIGN PATENT DOCUMENTS

WO   WO 00/66769 A2    9/2000
WO   WO 2009/054713 A2  4/2009
WO   WO 2012/162610 A1 11/2012

OTHER PUBLICATIONS

Tune et al. (JNCI, 1999, 91(9):796-800) (Year: 1999).*
(Continued)

*Primary Examiner* — Stephanie K Mummert
(74) *Attorney, Agent, or Firm* — Bereskin & Parr LLP; Ainslie B. Parsons

(57) ABSTRACT

Methods and devices for nasopharyngeal carcinoma screening are disclosed. The method comprises providing a nasopharyngeal sample from a subject, isolating DNA from the sample, amplifying and detecting at least one EBV target sequence from the DNA using real-time PCR, wherein a real-time PCR cycle threshold number of less than or equal to 31.5 is indicative of the subject having nasopharyngeal carcinoma or a risk of developing nasopharyngeal carcinoma. The device for obtaining a brush biopsy sample comprises a longitudinal shaft having a first end and a second end, wherein at least two brush heads extend from the second end of the shaft.

9 Claims, 19 Drawing Sheets

Specification includes a Sequence Listing.

(51) Int. Cl.
*A61B 10/02* (2006.01)
*C12Q 1/70* (2006.01)

(52) U.S. Cl.
CPC .............. *A61B 2010/0216* (2013.01); *C12Q 2600/118* (2013.01); *C12Q 2600/158* (2013.01)

(56) References Cited

U.S. PATENT DOCUMENTS

| | | | |
|---|---|---|---|
| 8,637,315 B2 * | 1/2014 | Durocher | C07K 14/005 435/320.1 |
| 2003/0040681 A1 * | 2/2003 | Ng | A61B 10/02 600/562 |
| 2004/0059253 A1 | 3/2004 | Martone | |
| 2008/0188769 A1 | 8/2008 | Lu | |
| 2009/0047657 A1 | 2/2009 | Iwatsuki | |
| 2013/0029319 A1 | 1/2013 | Schmitt et al. | |

OTHER PUBLICATIONS

Bell et al. (J Gen Virol, 2006, 87:2885-2890) (Year: 2006).*
Tong et al. (Clin Cancer Research, 2002, 8:2612-2619) (Year: 2002).*
Lowe et al. (Nucleic Acids Research, 1990, 18(7):1757-1761) (Year: 1990).*
Lin et al. (NEJM, 2004, 350:2461-2470) (Year: 2004).*
Lo et al. (Cancer Research, 1999, 59:1188-1191) (Year: 1999).*
"Risk Assessment for Nasopharyngeal Carcinoma (NPC)" NP Screen Assay, p. 1-12, obtained from Primex Lab website, 2006 (Year: 2006).*
Applied Biosystems, Application Note "Real-Time PCR: Understanding CT". May 2008.
Adham M et al., Epstein-Barr Virus DNA Load in Nasopharyngeal Brushings and Whole Blood in Nasopharyngeal Carcinoma Patients before and after Treatment. Clin. Cancer Res, Mar. 14, 2013, vol. 19, No. 8, pp. 2175-2186.
Ng R.H.W. et al., Trans-Oral Brush Biopsies and Quantitative PCR for EBV DNA Detection and Screening of Nasopharyngeal Carcinoma. Otolaryngol Head Neck Surg, Jan. 31, 2014, vol. 150, No. 4, pp. 602-609.
D'Souza, G. et al., "Analysis of the Effect of DNA Purification on Detection of Human Papillomavirus in Oral Rinse Samples by PCR", Journal of Clinical Microbiology, Nov. 2005, vol. 43, No. 11, p. 5526-5535.
Gulley M.L., "Molecular Diagnosis of Epstein-Barr Virus-Related Diseases", Journal of Molecular Diagnostics, vol. 3, No. 1, Feb. 2001, p. 1-10.
Lay, M-L. et al., "Measurement of Epstein-Barr virus DNA load using a novel quantification standard containing two EBV DNA targets on SYBR Green I dye", Virology Journal 2010, 7:252, p. 1-11.
Lo, Y.M. Dennis et al., "Quantitative Analysis of Cell-free Epstein-Barr Virus DNA in Plasma of Patients with Nasopharyngeal Carcinoma", Cancer Res 1999; 59:1188-1191.
Lo, Angela K.F. et al., "Epstein-Barr Virus Infection Alters Cellular Signal Cascades in Human Nasopharyngeal Epithelial Cells", Neoplasia, vol. 8, ni. 3, Mar. 2006, p. 173-180.
Makitie, A.A. et al., "Epstein-Barr virus DNA measured in nasopharyngeal brushings in patients with nasopharyngeal carcinoma: pilot study", J Otolaryngol. Oct. 2004;33(5):299-303 (Abstract only).
Real-time PCR: Understanding CT. Application Note [online]. Applied Biosystems by Life Technologies, 2011 [retrieved on Nov. 27, 2014]. Retrieved from the Internet: <URL:http://www.lifetechnologies.com/content/dam/LifeTech/migration/en/filelibrary/nucleic-acid-amplification-expression-profiling/pdfs.par.70657.file.dat/understanding%20ct%20application%20note.pdf>.
Risk Assessment for Nasopharyngeal Carcinoma (NPC). NP Screen Assay, p. 1-12 (2006). <URL:http://www.primexlab.com/lab/labpdfs/Primex%20Physician%20Web%20Site%20Info.pdf>.
Stevens, S. et al., "Noninvasive diagnosis of nasopharyngeal carcinoma: nasopharyngeal brushings reveal high Epstein-Barr virus DNA load and carcinoma-specific viral BARF1 mRNA", Electronic publication Mar. 29, 2006, International Journal of Cancer, 119(3):608-14.
Tong, J.H. et al., "Quantitative Epstein-Barr virus DNA analysis and detection of gene promoter hypermethylation in nasopharyngeal (NP) brushing samples from patients with NP carcinoma", Aug. 2002, Clinical Cancer Research, 8 (8):2612-19.
Sample Collection Swabs—Oasis Diagnostics Corporation, p. 1-2. <URL:http://4saliva.com/products/swabs.php>.

* cited by examiner

A.

B.

A.

B.

A.  B.  C.  D.

a.

b.

METHODS AND DEVICES FOR NASOPHARYNGEAL CARCINOMA SCREENING

CROSS-REFERENCE TO RELATED APPLICATIONS

The present application is a national phase entry of PCT/CA2014/000722 filed on Oct. 3, 2014 (which designates the U.S.) which claims the benefit of priority from U.S. provisional application No. 61/886,807 filed on Oct. 4, 2013 (now abandoned), the contents of which are incorporated herein by reference in their entirety.

INCORPORATION OF SEQUENCE LISTING

A computer readable form of the Sequence Listing "23192-P43305US01_SequenceListing.txt" (4,096 bytes), submitted via EFS-WEB and created on Mar. 30, 2016, is herein incorporated by reference.

FIELD OF THE DISCLOSURE

The disclosure relates to methods, compositions and devices for screening for nasopharyngeal carcinoma.

BACKGROUND

Nasopharyngeal cancer (NPC) is a highly prevalent malignancy of middle-aged subjects in endemic regions such as the Pacific and Mediterranean Rim Countries and subarctic regions. NPC is a major cause of death from disease in Southern China. Genetic and environmental factors contribute to tumor risk, and the high incidence and high population densities in NPC endemic areas make NPC a common cancer globally. The estimated global population at high risk is 1.3-1.5 billion people. There are approximately 500 new cases in North America, 5000 cases in Hong Kong and Taiwan and 100,000 cases worldwide annually (Ung 1999). NPC is an unusual cancer because of its close, near absolute association with the human gamma Herpes Virus 4, Epstein-Barr Virus (EBV), with each tumor cell harboring copies of the same viral clone, detectable already in early, pre-invasive lesions (Pathmanathan 1995). NPC arises in the remote retronasal space, where it can develop with little symptomatology, and not rarely is it first diagnosed in metastatic tissue, with consequently poor prognosis (Skinner 1990; Ho 1998). Despite growing incidence and awareness in the relevant populations, the reality of NPC is still dominated by late diagnosis, usually through nasopharyngoscopy, with good prognosis for tumors detected at an early stage (Liu 1998).

For decades, the close association between EBV and NPC has attracted attempts to improve the clinical diagnosis of NPC risk. Raab-Traub (1987) demonstrated all histological subsets of NPC contain EBV DNA. While large surveys of EBV serology delineated significant associations (e.g. Zeng 1986), the ubiquitous EBV carrier status of nearly all humans prevented EBV serology from attaining clinical utility (Ho 1998). Serology is highly sensitive but lacks specificity.

The diagnostic promise of retronasal biopsies with detection of EBV genomes by molecular biology means was first demonstrated in 1992 (Feinmesser 1992). While the molecular detection of EBV genomes in biological samples has become a robust routine, the transition from small academic research studies (Tune 1999) to routine ambulatory application has been difficult because of a lack of dedicated, single use biopsy instrumentation and the need for rapid, local DNA isolation to avoid DNA degradation. Both present challenges, in particular in endemic regions with varied levels of technological infrastructure.

SUMMARY

The present inventors have developed a highly specific and sensitive method for screening for nasopharyngeal cancer.

Accordingly, the present disclosure provides a method of detecting NPC or a risk of developing NPC in a test subject comprising (a) providing a nasopharyngeal sample, (b) isolating DNA from the sample and (c) amplifying and detecting at least one EBV target sequence from the DNA using real-time PCR, wherein a real-time PCR cycle threshold number of less than or equal to 31.5 is indicative of the test subject having NPC or a risk of developing NPC.

In one embodiment, a real time PCR cycle threshold number of 28 to 31.5 is indicative of the test subject having a risk of developing nasopharyngeal carcinoma.

In another embodiment, a real time PCR cycle threshold number of less than or equal to 28 is indicative of the test subject having nasopharyngeal carcinoma.

The cycle threshold (Ct) value may be used to calculate an Epstein-Barr Virus Detection Level (EDL). In particular, the Ct value can be used to determine the EBV copy number by using a standard curve that is generated with control EBV samples. The log of the EBV copy number provides the EDL. Table 14 demonstrates the correlation between the Ct value, EBV copies and the EDL.

In one embodiment, an EDL of greater than or equal to 2.7 indicates that a subject has NPC.

In another embodiment, an EDL of less than 1.7 indicates that the subject does not have NPC.

In a further embodiment, an EDV between 1.7 and 2.6 is an equivocal result and the test subject should be retested at a suitable interval, for example, 6 to 8 weeks.

In another embodiment, the nasopharyngeal sample is provided from a brush biopsy.

In another embodiment, the nasopharyngeal sample comprises epithelial cells.

In another embodiment, the at least one EBV target sequence is amplified from 40-60 ng, optionally about 50 ng of DNA.

In another embodiment, the at least one EBV target sequence is in the EBNA1 gene.

In another embodiment, the at least one EBV target sequence is amplified using primers corresponding to SEQ ID NO: 1 and 2.

In another embodiment, the at least one EBV target sequence is detected using a probe corresponding to SEQ ID NO: 4, wherein the probe is labeled with a reporter fluorophore at the 5'-end and a quencher fluorophore at the 3'-end.

The present inventors have also developed improved devices for obtaining brush biopsies. In one embodiment, the brush biopsy devices are for use in obtaining nasopharyngeal samples that can be used in the methods described herein.

Accordingly, the present disclosure provides a device for obtaining a brush biopsy sample comprising a longitudinal shaft having a first end and a second end, wherein at least two brush heads extend from the second end of the shaft.

In one embodiment, the at least two brush heads comprise a contact region connected to a brush shaft, the brush shaft extending from the second end of the shaft.

In another embodiment, the contact region comprises a sample collection surface.

In another embodiment, the sample collection surface comprises bristled surface, a serrated surface, a honey comb surface, a saw tooth surface or a porous surface.

In another embodiment, the at least two brush heads are connected to the second end of the shaft through a neck region.

In another embodiment, the neck region extends at an angle of 0 to 90 degrees, optionally about 65 to 75 degrees, to the longitudinal axis of the shaft.

In another embodiment, the brush heads extend from the neck region at an angle of 0 to 90 degrees, optionally about 65 to 75 degrees.

In another embodiment, the at least two brush heads are connected to each other through a brush connector region.

In another embodiment, the at least two brush heads are parallel to each other.

In another embodiment, the distance between the two brush heads is 0.5 cm to 5.0 cm, optionally about 1.0 to 2.0 cm.

In another embodiment, the two brush heads extend outwardly from the second end to form a V-shape.

In another embodiment, the angle of the V-shape is 10 to 150 degrees, optionally about 20 to 90 degrees.

In another embodiment, the distance between the two brush heads at the widest point of the V-shape is 0.5 to 5.0 cm, optionally 1.0 to 2.0 cm.

In another embodiment, the contact region is detachable from the brush shaft.

In another embodiment, the shaft is in the shape of a blade or a rod.

In another embodiment, the shaft is 5 to 30 cm in length or optionally about 13 to 19 cm in length.

The present disclosure also provides a device for obtaining a brush biopsy sample comprising a longitudinal shaft having a first end and a second end and at least one brush head extending from the second end of the shaft, wherein the at least one brush head is moveable between a first uninflated position and a second inflated position.

In one embodiment, the brush head is unelongated in the first uninflated position and elongated in the inflated elongated position.

In another embodiment, the brush head is 1 to 10 centimeters, optionally 3 to 7 cm, longer in the second elongated position than in the first unelongated position.

In another embodiment, the brush head comprises an inflatable contact region and a brush shaft.

In another embodiment, the contact region of the brush head comprises a sample collection surface for providing a biopsy sample.

In another embodiment, the sample collection surface comprises less than 50%, 40%, 30%, 20% or 10% of the contact region.

In another embodiment, the sample collection surface is interior to the contact region in the first uninflated position and exterior to the contact region in the second inflated position.

In another embodiment, the sample collection surface comprises a bristled surface, a brush surface, a serrated surface, a honey comb surface, a saw tooth surface or a porous surface.

In another embodiment, the shaft comprises a means for inflating the brush head.

In another embodiment, the shaft is connected to a handle, the handle comprising a means for inflating the brush head.

In another embodiment, the handle is detachable from the shaft.

In another embodiment, the device comprises a handle extending from the first end of the shaft, the handle comprising a light.

In another embodiment, the light is oriented to provide illumination along the longitudinal axis of the shaft.

In another embodiment, the handle is detachable from the shaft

In another embodiment, the first end of the shaft is insertable into a receptacle on the handle.

The disclosure also provides method of providing a nasopharyngeal sample from a subject, the method comprising contacting the nasopharynx of a subject with any one of the devices describe herein. In one embodiment, the method is performed transorally.

The disclosure also a method of providing an oral, oropharynx or hypopharynx sample from a subject, the method comprising contacting the oral cavity, oropharynx or hypopharynx of a subject with the devices described herein.

BRIEF DESCRIPTION OF THE DRAWINGS

The disclosure will now be described in relation to the drawings in which.

DETAILED DESCRIPTION

Methods of the Disclosure

Figure 1:
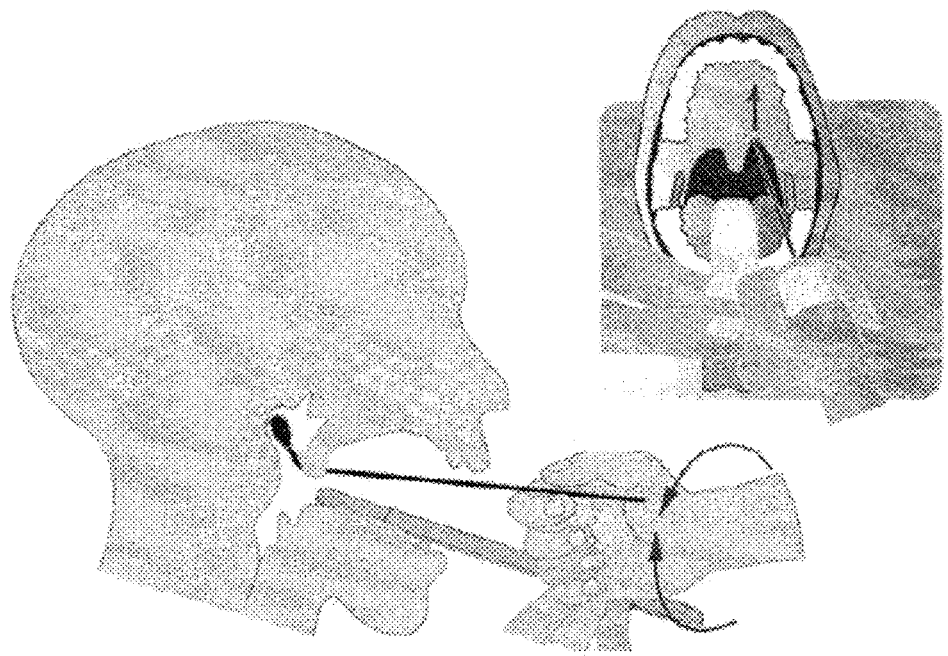
FIG. 1 shows a transoral brushing procedure. (A) With a gentle forward pressure, the brush is pressed against the nasopharynx wall and brushing motion is initiated to collect epithelial cell samples from the nasopharynx surface. (B) A trans-oral brushing device.
Figure 1:

The present inventors have developed a highly specific and sensitive method for screening for nasopharyngeal cancer.

Accordingly, the disclosure provides a method of detecting nasopharyngeal carcinoma or a risk of developing nasopharyngeal carcinoma in a test subject comprising:
  a. providing a nasopharyngeal sample from the subject,
  b. isolating DNA from the sample,
  c. amplifying and detecting at least one EBV target sequence from the DNA using real-time PCR,
  wherein a real time PCR cycle threshold number of less than or equal to 31.50 is indicative of the test subject having nasopharyngeal carcinoma or a risk of developing nasopharyngeal carcinoma.

As used herein, the term "nasopharyngeal cancer" or "nasopharyngeal carcinoma" (NPC) refers to a malignant neoplasm, or cancer, arising from the mucosal epithelium of the nasopharynx. Staging of nasophayngeal carcinoma is based on clinical and radiologic examination: Stage I is a small tumor confined to nasopharynx, Stage II is a tumor extending in the local area, or that with any evidence of limited neck (nodal) disease, Stage III is a large tumor with or without neck disease, or a tumor with bilateral neck disease and Stage IV is a large tumor involving intracranial or infratemporal regions, an extensive neck disease, and/or any distant metastasis. Nasopharyngeal carcinoma is associated with infection with Epstein-Barr virus (EBV).

Epstein Barr virus (EBV) is a human DNA tumor virus. Each NPC tumor cell carries episomal copies of EBV which contribute to tumor development.

As used herein, the expression "detecting nasopharyngeal cancer" also refers to detecting nasopharyngeal cancer in a pre-symptomatic subject. "Detecting nasopharyngeal cancer" also includes detecting the severity, progression, and/or stage of the nasopharyngeal cancer, or the presence of local or regional recurrences post radiation or chemotherapy.

The expression "detecting nasopharyngeal cancer" also includes predicting the prognosis, treatment outcome as well as survival duration of nasopharyngeal cancer.

As used herein, the expression "providing a nasopharyngeal sample" refers to any means by which a sample or biopsy of the nasopharnx is obtained from a subject. The nasopharynx is the upper most part of the pharynx. Methods of providing or obtaining nasopharyngeal samples are well known in the art.

"Providing a nasopharyngeal sample" includes providing or obtaining a sample of tissue and/or cells from the surface of the nasopharynx. In one embodiment, the cells are epithelial cells such as squamous epithelial cells and respiratory epithelial cells. In other embodiments, the cells are lymphoid cells (lymphocytes) or blood cells.

Samples can be obtained either transnasally or transorally. In a preferred embodiment, samples are obtained transorally as this is a relatively comfortable and a non-traumatic means of access to the nasopharynx with minimal or no bleeding compared to the transnasal route which can be uncomfortable and difficult to perform in patients. In the trans-nasal approach involves biopsy through the anterior and posterior nasal cavities from both sides of the nasopharynx through the nose. The trans-oral approach accesses both sides of the nasopharynx equally through one access point.

In one embodiment, a sample of tissue and/or cells, preferably epithelial cells, are obtained from the nasopharynx using a brush or a swab. A sample of tissue and/or cells obtained using a brush is also referred to as a "brush biopsy". Examples of brush biopsy devices for obtaining nasopharyngeal samples are described in more detail below.

The present methods include isolating DNA from the nasopharyngeal sample. In one embodiment, the DNA is total DNA. Methods of isolating or extracting DNA from a tissue or cell sample are well known in the art. For example, DNA may be extracted using commercial kits such as the MagNA Nucleic Acid Isolation Station and the MagNA Pure LC DNA IsolationKit from Roche Diagnostics. In another example, DNA is extracted using a DNA extraction robot such as the Qiagen automated DNA extraction from model 9604.

Following extraction, the DNA is optionally quantitated and normalized to a specific concentration. Methods of DNA quantitation are well known in the art. For example, DNA is optionally quantitated using fluorometic binding dye in combination with fluorometry. In one embodiment, the DNA concentration is normalized to 8-12 ng/µl, optionally 10 or about 10 ng/µl.

The present methods include performing real-time PCR on the DNA. In a preferred embodiment, real-time PCR is performed on the DNA after it has been normalized to a specific concentration. In one embodiment, real-time PCR is performed on about 5 µL aliquots of about 10 ng/µl or 50 ng of DNA total. A person of skill in the art will appreciate that other DNA concentrations (for example, 1 to 50 ng/µl, optionally 5 to 20 ng/µl) and amounts (for example, 10 to 100 ng, optionally 25 to 75 ng of DNA) can be used.

"Real-time PCR" or "Real-time polymerase chain reaction" is a method used to both used to amplify and simultaneously quantify a nucleic acid sequence. The procedure follows the general principle of polymerase chain reaction (PCR). PCR is well known to people skilled in the art. PCR relies on cycles of repeated heating and cooling of the reaction for DNA melting and enzymatic replication of the nucleic acid. Primers containing sequences complementary to the target region along with a DNA polymerase enable selective and repeated amplification. As PCR progresses, the DNA generated is itself used as a template for replication and thus the DNA template is exponentially amplified as the reaction progresses. In real-time PCR, the products of the reaction are detected as the reaction proceeds. Two common methods for the detection of products in real-time PCR are: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary DNA target.

As used herein, the term "EBV target sequence" refers to a nucleic acid sequence present in the EBV genome. An example of an EBV genome sequence is the EBV B95.8 genome sequence with GenBank Accession No. V01555. An EBV target sequence is optionally 10-200, 15-150, 20-120, 30-110, 40-100, 50-90, 60-85 or 70-80 nucleic acid residues in length. In one embodiment, an EBV target sequence is a nucleic acid sequence present in the EBV genome but not present in the genome of the subject. In another embodiment, an EBV target sequence is a nucleic acid sequence present in an EBV gene known to encode a viral protein expressed in EBV-related malignancies such as nasopaharyngeal cancer. Examples of EBV target sequences include sequence contained within the EBNA1 gene. EBNA1 is also known as Epstein-Barr nuclear antigen 1 and encodes for an EBV viral protein.

EBNA1 sequences can be found, for example, within the following EBV genomes:
  Human herpesvirus 4 complete wild type genome
    171,823 bp circular DNA
    Accession:AJ507799.2; GI:86261677
  Epstein-Barr virus (EBV) genome, strain B95-8
    172,281 bp circular DNA
    Accession:V01555.2; GI:94734074
  Human herpesvirus 4 type 1, complete genome
    171,823 bp circular DNA
    Accession:NC_007605.1; GI:82503188
  Human herpesvirus 4 strain Mutu, complete genome
    171,687 bp circular DNA
    Accession:KC207814.1; GI:428161102

Other examples of EBV target sequences include sequences contained within other EBV genes including, but are not limited to, EBV nuclear antigen 2 (EBNA2), EBNA-3A, EBNA-3B, EBNA-3C, EBNA-LP, LMP-1 (EBV latent membrane protein 1), LMP-2A, LMP-2B and EBER (EBER1 and EBER2; small nuclear RNAs associated with the Epstein-Barr virus).

A person of skill in the art would readily understand how to design primers for amplifying an EBV target sequence by real-time PCR. The term "primer" as used herein refers to a nucleic acid sequence which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less, for example, up to 5, 10, 12 or 15 nucleotides. The factors involved in determining the appropriate length of primer are readily known to one of ordinary skill in the art.

Examples of primers useful for amplifying an EBV target sequence within EBNA1 include SEQ ID NO: 1 (5'-GTC GTC TCC CCT TTG GAA TG-3') and SEQ ID NO: 2 (5'-AAT AAC AGA CAA TGG ACT CCC TTA GC-3'). SEQ ID NOs: 1 and 2 amplify a 75 basepair fragment of EBNA1 (SEQ ID NO: 3; GTCGTCTCCCCTTTGGAATGGC-CCCTGGACCCGGCCCACAACCTGGCCCGCTAAG GAGTCCATTGTCTGTTATT).

A person of skill in the art would also readily understand how to design a probe for detecting an EBV target by real-time PCR. The term "probe" as used herein refers to a nucleic acid sequence that will hybridize to an EBV target sequence. A person of skill in the art will understand that an EBV probe should be designed to detect a sequence falling within the amplified sequence (for example, a region located between the forward and reverse primers). The length of probe depends on the hybridization conditions and the sequences of the probe and EBV target sequence. In one embodiment, the probe is at least 8, 10, 15, 20, 25, 50, 75, 100, 150, 200, 250, 400, 500 or more nucleotides in length.

The term "hybridize" refers to the sequence specific non-covalent binding interaction with a complementary nucleic acid. In one embodiment the hybridization is conducted under at least moderately stringent conditions. In a preferred embodiment, the hybridization is under at least moderately stringent hybridization conditions.

By "at least moderately stringent hybridization conditions", it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)− 600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% sequence identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5x sodium chloride/sodium citrate (SSC)/5×Denhardt's solution/1.0% SDS at Tm-5° C. based on the above equation, followed by a wash of 0.2×SSC/0.1% SDS at 60° C. for 15 minutes. Moderately stringent hybridization conditions include a washing step in 3×SSC at 42° C. for 15 minutes. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 2000, Third Edition.

The probe for detecting an EBV target includes a detectable label. In one embodiment, the probe is labeled with a flourophore (a flourogenic probe). In a further embodiment, the probe includes both a reporter at one end of the probe and a quencher at the other end of the probe. On example of a fluorogenic probe useful is the present methods is the TaqMan probe which is a dually labeled with a reporter (FAM) at the 5' end and a quencher (TAMRA) at the 3' end. The sequence of one TaqMan probe useful for detecting an EBV target sequence is SEQ ID No: 4 (5'-(FAM) CCT GGA CCC GGC CCA CAA CC (TAMRA)-3'). SEQ ID No: 4 detects a region of the EBNA 1 gene located between the forward and reverse primers, SEQ ID NO: 1 and 2, respectively.

Other probes useful in the present methods can have different design and flour combinations. Examples include MGB probes and Scorpion probes. In one embodiment, the fluorogenic probe does not fluoresce unless the fluor is cleaved or it is separated from its quencher. Other fluors/reporters that can be used include, but are not limited to, VIC, Tamra and SYBR green.

In another embodiment, an internal control is co-amplified and detected during the real-time PCR reaction. The internal control is optionally a target sequence contained in a human gene such as the RNaseP gene. A person of skill in the art could readily design primes and probes to the internal control. In one example the TagMan RNaseP Detection Reagent kit is used to amplify and detect a RNaseP gene target sequence.

During real-time PCR, the EBV target sequence is amplified and detected. In one embodiment, the PCR amplification cycles are 2'/50° C., 5'/95° C., 40×{20"/95° C., 60"/62° C.}.

PCR can have many variant conditions. A person of skill in the art would readily be able to optimize the PCR reaction. For example, reaction volumes can vary from 5 μls to 200 μls. In other embodiments, the hybridization times can vary from 10 seconds to 1 minute and the hybridization temperature can vary from 50° C. or lower to up to 72° C.

As used herein, the term "Ct" refers to the cycle threshold number. The cycle threshold number is the PCR cycle at which the signal from the amplified sequences is first recorded as statistically significant above background signal. The more target sequences present in the starter template, the fewer PCR cycles it will take for the fluorescence intensity to cross the threshold. A person of skill in the art will appreciate that the Ct value for an EBV target sequence will depend on the unique emission spectrum of the fluorogenic probe being used for detection. In one embodiment, the Ct values for an EBV target sequence are the Ct values for the TaqMan probe (Ct(FAM)).

The Ct value for an EBV target sequence indicates if a subject has NPC or is at risk of developing NPC. In one embodiment, a Ct value of less than 31.50 indicates that a subject has NPC. A Ct value of greater than 31.50 indicates that a subject does not have NPC, or there is a low likelihood that the subject has NPC.

In another embodiment, a Ct value between 31.50 and 40.00 indicates a low likelihood of EBV associated NPC. In the absence of other clinical findings, the subject is considered normal although the subject should likely be retested after an appropriate interval, e.g. 6 to 8 weeks.

In another embodiment, a Ct value between 28.00 and 31.50 indicates that a subject is at a higher risk than normal to develop NPC.

In another embodiment, a Ct value of less than 28.00 indicates that a subject has NPC.

The Ct value may be converted into an Epstein-Barr Virus Detection Level (EDL). In particular, the Ct value can be used to determine the EBV copy number as the Ct number is inversely proportional to the EBV number as the more EBV present in the sample, the fewer PCR cycles it takes to detect the EBV. Once the Ct value is determined it can be correlated with an EBV copy number using a standard curve that is generated with control EBV samples. The log of the EBV copy number provides the EDL. Table 14 demonstrates the correlation between the Ct value, EBV copies and the EDL.

Accordingly, the disclosure also provides:
a. providing a nasopharyngeal sample from the subject,
b. isolating DNA from the sample,
c. amplifying and detecting at least one EBV target sequence from the DNA using real-time PCR, and
d. calculating the EDL and determining whether or not the test subject has or is at risk for developing nasopharyngeal cancer.

In one embodiment, an EDL of greater than or equal to 2.7 indicates that a subject has NPC.

In another embodiment, an EDL of less than 1.7 indicates that the subject does not have NPC.

In a further embodiment, an EDL between 1.7 and 2.6 is an equivocal result and the test subject should be retested at a suitable interval, for example, 6 to 8 weeks.

The methods described herein are also applicable to detecting other types of cancer, carcinomas or a risk of developing other types of cancers in a test subject. In one embodiment, the methods described herein are used to detect the presence of oropharyngeal cancer in a subject. The oropharynx is the middle part of the pharynx and includes the back third of the tongue, side and back walls of the throat and the tonsils. Oropharyngeal cancer is a cancer of epithelial cells that occurs in that area. Approximately 70% of oropharyngeal cancers are associated with Human Papillaform Virus (HPV), specifically strain HPV 16.

In another embodiment, the methods described herein are used to detect the presence of cancer in the oral cavity in a subject. The oral cavity is the part of the cavity that includes the tongue, side walls of the oral cavity (buccal mucosa), the hard and soft palates, floor of mouth and gingiva.

In another embodiment, the methods described herein are used to detect the presence of cancer in the hypopharynx and/or larynx in a subject. The hypopharynx is the lower part of the pharynx below the tongue base adjacent to the larynx. The larynx consists of the vocal cords and areas above (supraglottis) and below (sub-glottis).

Accordingly, in one embodiment of the present disclosure, a method of detecting oral, oropharyngeal, hypopharynx and/or larynx cancer or a risk of developing oral, oropharyngeal, hypopharynx and/or larynx cancer in a test subject is provided, the method comprising:
a. providing an oral, oropharyngeal, hypopharynx or larynx sample from the subject,
b. isolating DNA from the sample,
c. amplifying and detecting at least one HPV 16 target sequence from the DNA using real-time PCR, wherein a real time PCR cycle threshold number less than or equal to a specific number is indicative of the test subject having oral and/or oropharyngeal, hypopharyngeal or laryngeal cancer.

In one embodiment, the cycle threshold number is converted to the EDL which is used to determine whether or not the test subject has oral and/or oropharyngeal, hypopharyngeal or laryngeal cancer.

The HPV 16 target sequence is optionally amplified and detected using an HPV 16 primers and probes, for example, those provided by Geneprobe and Roche.

In a further embodiment, the oral, oropharyngeal, hypopharynx and/or larynx sample is obtained using a brush biopsy device as described herein.

Brush Biopsy Devices

The present inventors have developed novel devices for obtaining biopsy samples. Accordingly, the disclosure provides brush biopsy devices specially designed for harvesting tissue and/or cells from a body surface such as the nasal cavity, nasopharynx, oral cavity, oropharynx, hypopharynx and larynx.

As described above, nasopharyngeal cancer (NPC) originates in the nasopharynx. The nasopharynx is the upper most part of the pharynx and can be difficult to access and visualize without proper training and the use of special medical instruments such as an endoscope.

In one embodiment, the devices described herein are for use in obtaining a biopsy sample, preferably a brush biopsy sample, from the nasopharynx. As used herein, the term "brush biopsy sample" refers to the collection of cells and/or tissue by means of brushing or scraping a body surface with a brush or swab to remove cells and/or tissue from the area being sampled.

In other embodiments, the devices are for use in obtaining a brush biopsy sample from the cervix, the oropharynx, the oral cavity, the tongue base, the tonsillar areas, the vallecular and/or the hypopharynx. The devices can be used for the sampling and/or retrieval of various cell types from any of the aforementioned regions, including, but not limited to lymphoid cells, epithelial cells and mucosal cells. Once cell samples are obtained, cellular cytologic analysis can be performed to determine the presence or absence of cancer. For example, in addition to retrieving samples from the nasopharynx for the detection of Epstein Barr Virus and the detection of nasopharyngeal carcinoma, the devices described herein can also be used to retrieve samples for detection of Human Papilloma Virus DNA and detection of oral, oropharynx hypopharynx and/or larynx cancer. The devices can also be used to detect presence of squamous cell carcinoma, papilloma or other virally induced tumors. The devices can also be used to detect bacteria and viruses. In other embodiments, the devices can be used to brush the surface of the tonsils for retrieval of samples for cytogenetic or flow cytometry studies for detection of lymphoma or other lymphoproliferative disorders. The devices can also be used to brush the oral cavities and oropharynx for detection of Epstein Barr Virus for diagnosis of mononucleosis.

Bifurcated Brush Biopsy Device

One limitation of the prior art devices for obtaining biopsy samples from the nasopharynx is that they only allow collection at a single site. In cases where NPC is in its early stages, not all surfaces of the nasopharynx necessarily contain cancerous cells. Obtaining a sample from more than one area of the nasopharynx increases the likelihood that nasopharyngeal cancer, particularly early stage nasopharyngeal cancer, can be detected using the methods described herein. The devices described below allow biopsy samples to be taken from two different areas of the nasopharynx at the same time. In particular, the bifurcated brush head allows the device to access both areas of the fossae of Rosenmuller, also known as the posterolateral recess of the nasopharynx, where NPC commonly occurs.

Figure 8:
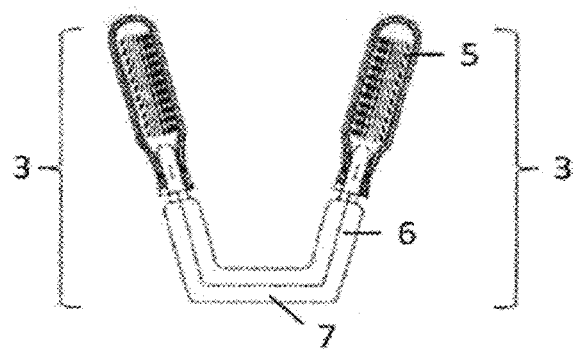
FIG. 8 shows a brush biopsy device having a bifurcated brush head. (A) is an enlarged view of the bifurcated brush head of the brush biopsy device (B).
Figure 8:
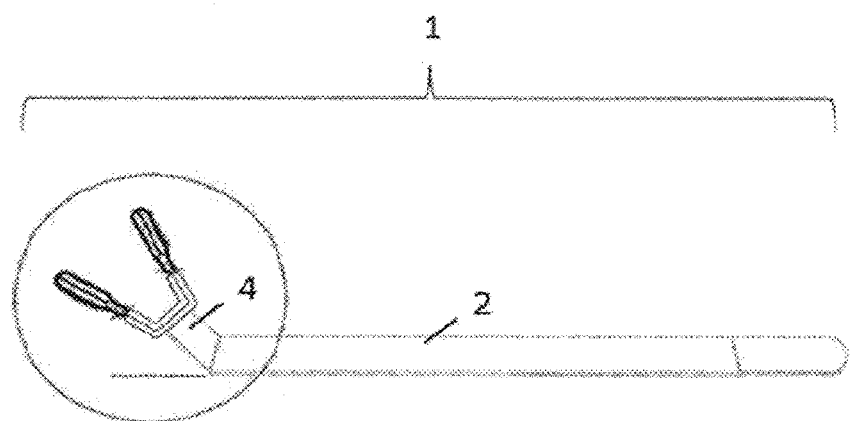

Referring to FIG. 8, a brush biopsy device 1 is shown having a bifurcated brush head. The device has a longitudinal shaft 2 and two brush heads 3 which comprise the bifurcated brush head. The brush heads 3 are connected to the shaft 2 through neck region 4. The brush heads comprise a contact region 5 and a brush shaft 6. The contact region 5 is for obtaining a biopsy sample from the nasopharynx or other anatomical region. The brush shaft 6 is connected to the neck region 4. In one embodiment, each brush head 3 extends from the neck region 4 via a brush connector region 7 extending roughly perpendicular to the neck region 4. In another embodiment, the brush heads 3 extend directly from the shaft without the use of a neck region and/or a brush connector region.

Figure 9:
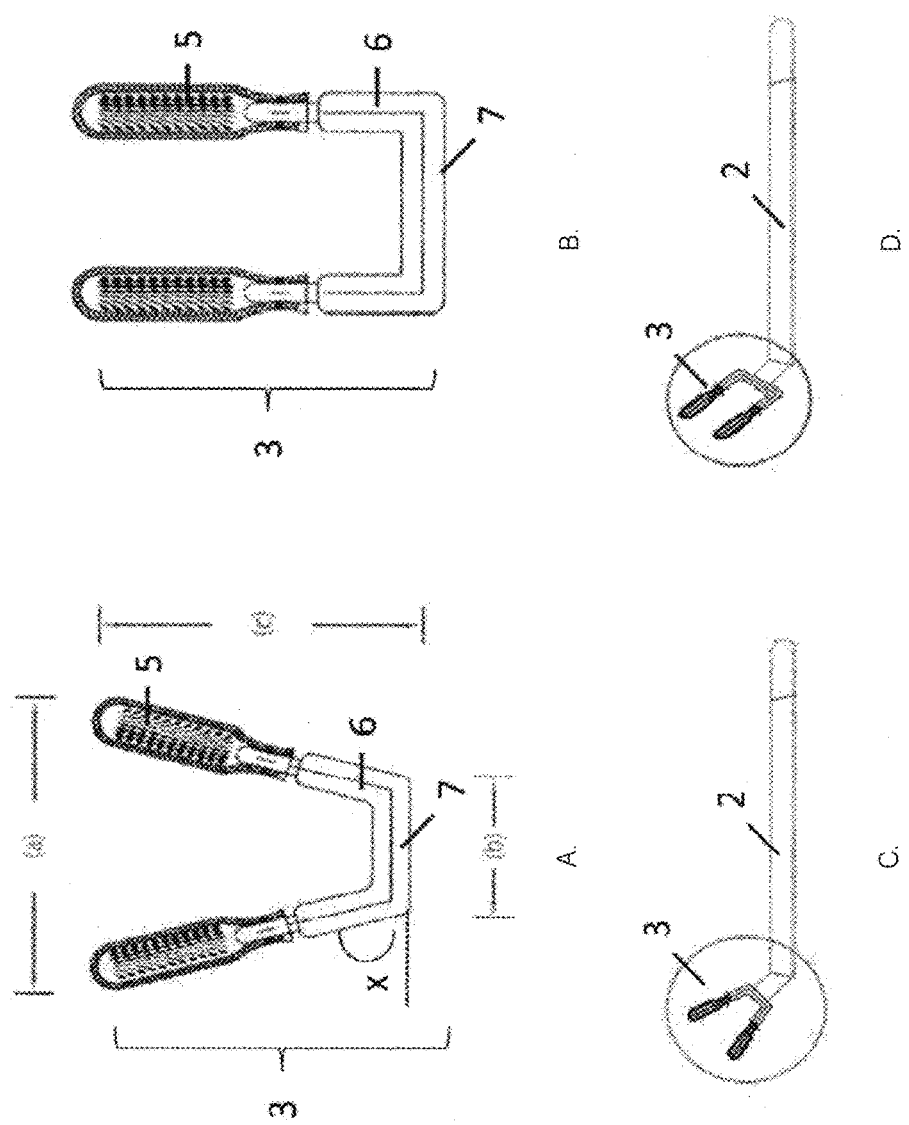
FIG. 9 shows different configurations of a bifurcated brush head. (A) and (B) show a non-parallel bifurcated brush head. (A) is an enlarged view of the non-parallel bifurcated brush head of the brush biopsy device of (B). (C) and (D) show a parallel bifurcated brush head. (C) is an enlarged view of the parallel bifurcated brush head of the brush biopsy device of (D).

Referring to FIG. 9, different configurations of the brush heads 3 are possible. As shown in FIGS. 9(a) and (b), the brush heads 3 may extend in a non-parallel or "V-shape" away from each other such the contact regions 5 of the two brush heads are further apart from each other than the brush shafts 6 of the two brush heads. In one embodiment, one or both of the brush heads extend at an angle (x) from brush connector region 7. The angle (x) is optionally less the 90 degrees, optionally 45 to 85 degrees. In another embodiment, the two brush heads extend at an angle of 10 to 150 degrees from each other, optionally 20 to 90 degrees. In one embodiment, the distance (a) between the two brush heads at the widest point of the V-shape is 0.5 to 5.0 cm, optionally 1.0 to 2.0 cm. In one embodiment, the distance (b) between the two brush heads at the narrowest part of the V-shape ranges is 0.1 cm to 5 cm, optionally 0.2 to 1 cm or about 0.2 or 0.5 centimeters. In another embodiment, the distance (b) between the two brush heads at the narrowest part of the V-shape corresponds to the width of the shaft 2. The vertical length (c) of the brush heads is optionally 1 to 5 cm or 2 to 3 cm, optionally about 3 cm.

As shown in FIGS. 9(c) and (d), in another embodiment the brush heads 3 extend parallel to each other. In one embodiment, the distance between the two brush heads 3 optionally ranges from 0.5 cm to 5 cm, optionally about 1.0 to 2.0 centimeters. In another embodiment, the distance between the two brush heads corresponds to the width of the shaft. The vertical length of the brush heads is optionally 1 to 5 cm or 2 to 3 cm, optionally about 3 cm.

The contact region 5 can take any shape useful for obtaining a biopsy sample. In one embodiment, the contact region is in the shape of a rod or cylinder. In another embodiment, the contact region in the shape of a blade.

Figure 10:
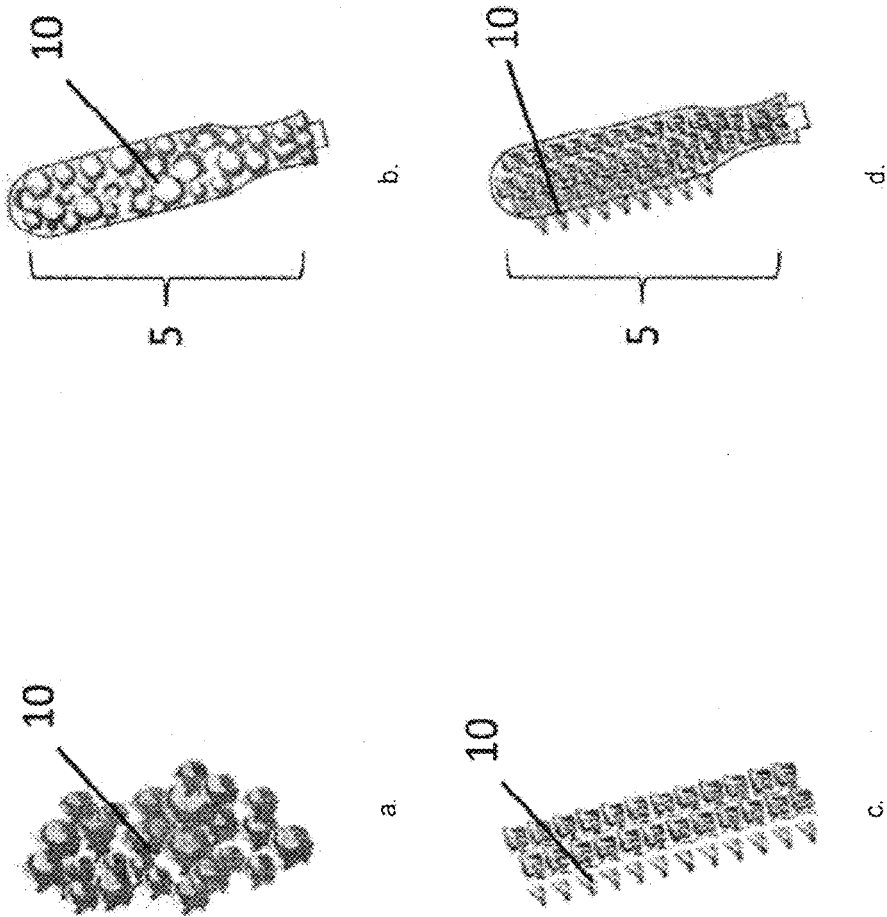
FIG. 10 shows various surfaces that can be used on a brush biopsy device for collecting sample. (A) shows a porous surface, (B) shows a honey comb circumferential surface, (C) and (D) show a serrated or sawtooth surface.

Various embodiments of the contact region 5 are shown in FIG. 10. The contact region 5 can include any sample collection surface 10 useful for obtaining a tissue and/or cell sample from a body surface such as the nasopharynx. Examples of useful sample collection surfaces 10 include a bristled surface, a brush surface, a porous surface as shown in FIG. 10a, a honey comb surface as shown in FIG. 10(b) and a serrated or sawtooth surface as shown in FIGS. 10(c) and (d). The sample collection surface 10 optionally covers only a portion of the contact region (for example less than 50%, 40%, 30%, 20% or 10% of the contact region, one side of the contact region (see for example surface 10 in FIG. 14) or optionally extends over the entire contact region (for example in a circumferential arrangement as shown in FIG. 10(b)). Various materials can be used for the sample collection surface 10, including, but not limited to plastic, polymer, fine steel wires, nylon, carbon steel, coppers, silicon impregnated nylon and tynex.

Figure 11:
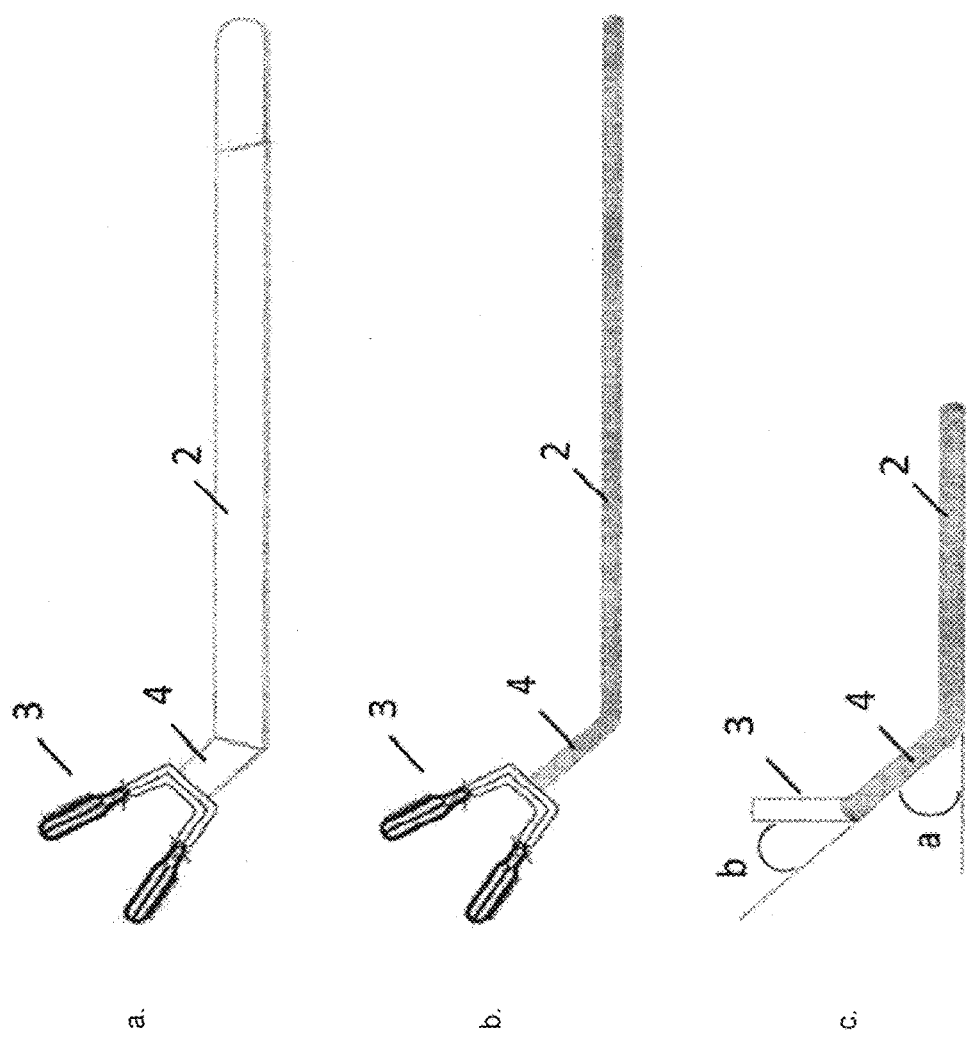
FIG. 11 shows various shafts that can be used with the brush biopsy devices. (A) depicts a blade, (B) depicts a rod and (C) details angles of the neck connector region and the brush heads.

Different shafts can be used with the brush biopsy devices described herein. In one embodiment, as shown in FIG. 11(a), the shaft 2 has a shape of a blade. The blade is predominantly flat with a width (w). The width (w) is optionally 1 to 5 cm, optionally 2 to 4 cm or about 3 cm. In one embodiment, the neck region 4 is of a similar width to the shaft 2. In another embodiment, as shown in FIG. 11(b), the shaft 2 has a shape of a rod. In one embodiment, the length of the shaft 2 is 5 to 30 cm, optionally 13 to 19 cm and preferably about 15 cm. In another embodiment, the neck region 4 is rod shaped and optionally of a similar diameter to the shaft 2. Various materials can be used for the shaft and/or the neck region such as plastics or metals. In one embodiment, the shaft is rigid or semi-rigid. In another embodiment, the shaft is bendable with compliance.

As depicted in FIG. 11(c), the neck region 4 optionally extends from the shaft 2 at an angle (a). The angle (a) is optionally 0 to 90 degrees or 0 to −90% (ie. pointing down) and is preferably 65 to 75 degrees (or −65 to 75 degrees in the downward direction). As further shown in FIG. 11(c), the brush heads 3 optionally extend from the neck region 4 at an angle (b). The angle (b) is optionally 0 to 90 degrees and is preferably 65 to 75 degrees. The angled brush head facilitates the collection of a sample from the nasopharynx, oropharynx or hypopharynx. In one embodiment, the neck region 4 is of a similar width to the shaft 2.

Figure 12:
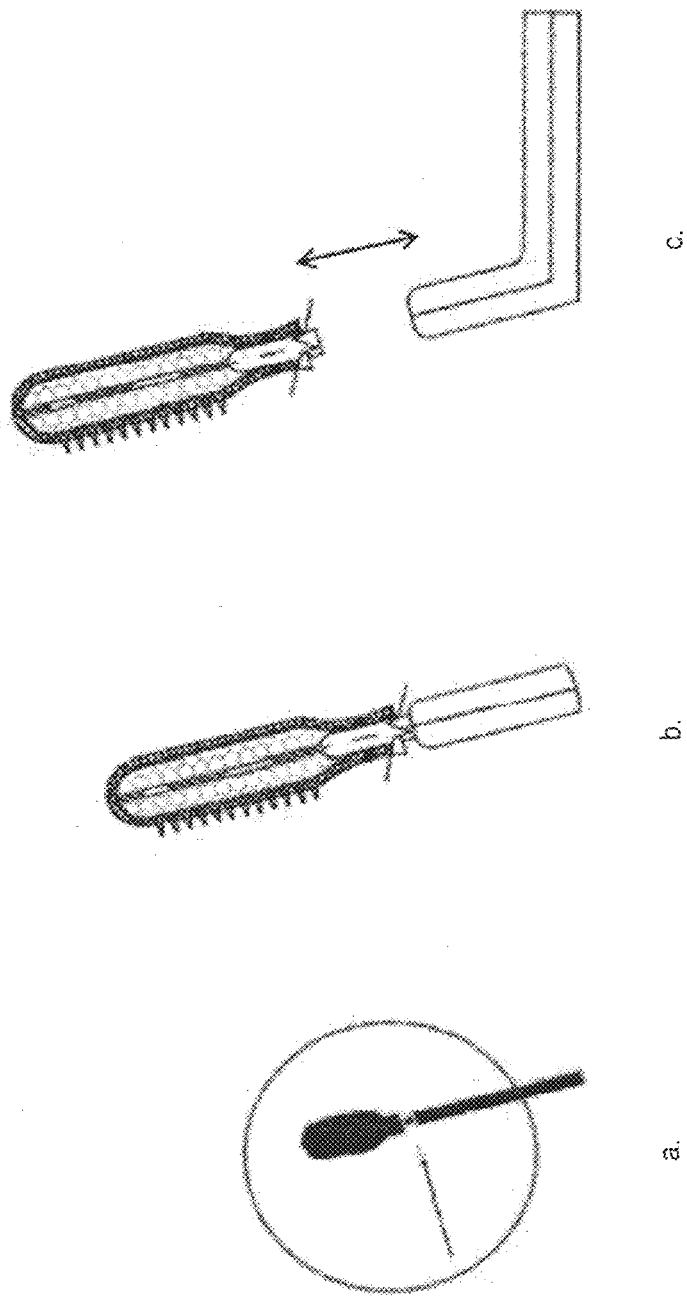
FIG. 12(A-C) shows a detachable brush head.

The brush heads and/or the contact region 5 are optionally detachable from the biopsy device after a sample has been collected. The contact region may be detached from the brush shaft (as shown for example in FIG. 12(a)-(c)) or the entire brush head may be detached from the rest of the biopsy device. Once detached, the brush head and/or the contact region can be stored in a composition such a transport buffer.

Inflatable Brush Biopsy Device

Figure 13:
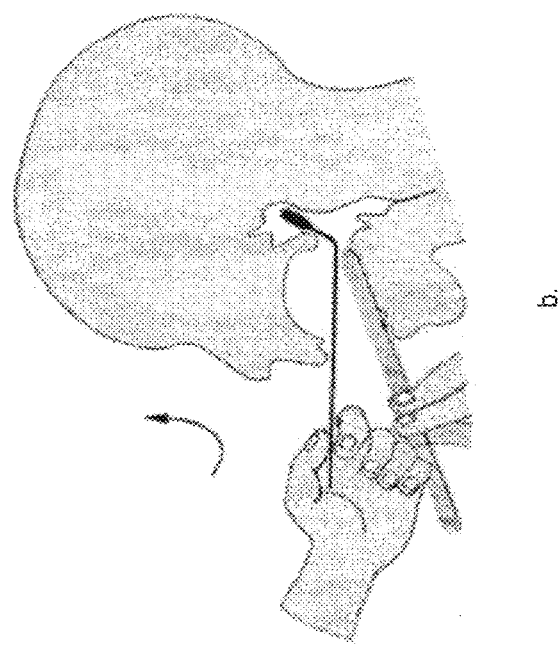
FIG. 13 depicts an inflatable brush head in use. (A) depicts the inflatable brush head before inflation (below the nasopharynx) and (B) depicts the inflatable brush head after inflation (inside the nasopharynx).
Figure 13:
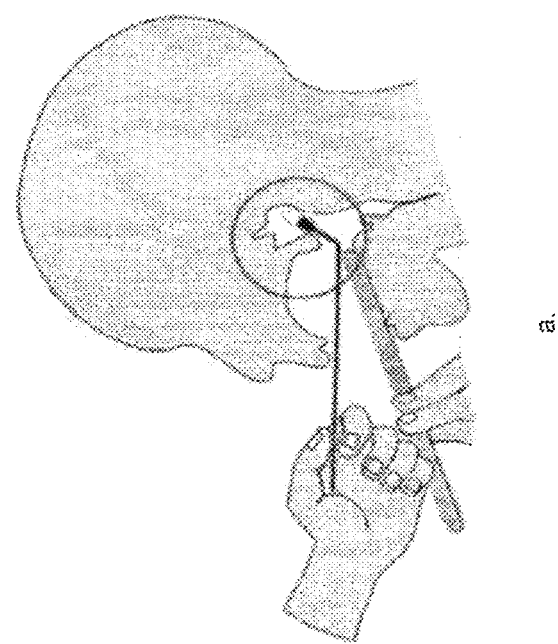

Another difficulty in obtaining biopsy samples from the nasopharynx or the oropharynx is that it can be difficult to access the sample collection site while ensuring minimal discomfort or gag reflex for the patient. Described herein is a brush biopsy device comprising a longitudinally extendable inflatable brush head. As shown in FIG. 13, the brush biopsy device can be inserted into a patient in its uninflated form (FIG. 13(a)). Once correctly positioned in the patient, the brush head can be inflated such that the brush head is extended/lengthened to allow entering of the nasopharynx (FIG. 13(b)), or similarly, in the hypopharynx.

Advantages of the inflatable brush biopsy device described herein over those in the prior art includes the elongating or lengthening of the brush to allow it to enter the nasopharynx or the orophaynx. In one embodiment, the extension is specific for the nasopharynx which is 3-7 cm long. Another advantage is that in one embodiment, the sample collection surface is only revealed when the brush is in its inflated/extended position. This configuration minimizes surface contact to tissues of the pharynx prior to biopsy and reduces the chance of a gag reflex. Further, in another embodiment, the sample collection surface is on one side of the brush head only. This configuration allows for single surface brushing which minimizes injury to the soft palate, or other areas of the pharynx not intended for biopsy.

In another embodiment, the extension is specific for the oropharynx, which is 3-10 cm long.

Figure 14:
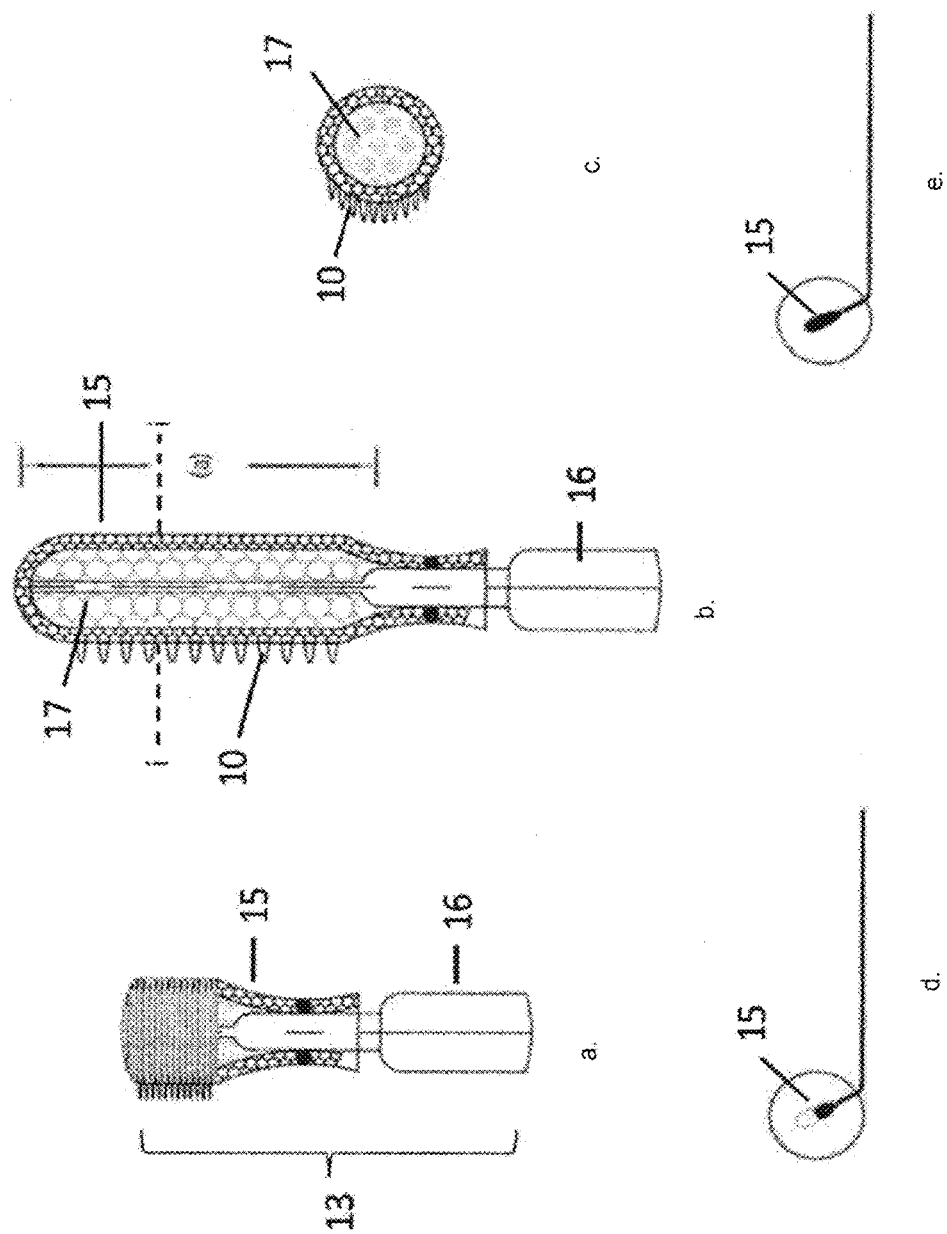
FIG. 14 depicts an inflatable brush head in its uninflated ((A) and (D)) and inflated ((B) and (E)) forms. (C) is a cross-sectional view of the inflated brush head of FIG. 13(B), taken along lines i-i.

Referring to FIG. 14, an inflatable brush head 13 is shown. The inflatable brush head comprises an inflatable contact region 15 and a brush shaft 15. The inflatable contact region 15 is shown in FIGS. 14(a) and (e) in its uninflated form and in FIGS. 14(b) and (f) in its inflated form. In its inflated form, the contact region 15 is optionally 1 to 10 or 3 to 7 cm longer than in its uninflated form. In another embodiment, the contact region 15 extends by a length that corresponds to the length of nasopharyngeal cavity, the hypopharynx or the oropharynx.

With reference to FIG. 14(c), the contact region optionally comprises a sample collection surface 10 on contact region 15. The sample collection surface 10 can include any surface useful for obtaining a tissue and/or cell sample from a body surface such as the nasopharynx. The contact region also optionally includes an interior air chamber 17 which is inflated to allow lengthening/extension of the brush head 13. FIG. 14(d), which is a cross section of the contact region taken along lines i-i of FIG. 14(b), depicts a sample collection surface 10 comprising a serrated surface. The sample collection surface 10 extends only partially around the contact region 15. In one embodiment, the sample collection surface for contacting the nasopharynx is on one side of the contact region. Having only a single surface for brushing as opposed to a circumferential surface can minimize injury to the soft palate or the lateral wall of the pharynx. In another embodiment, the sample collection surface 10 extends over the entire contact region (for example in a circumferential arrangement).

Figure 15:
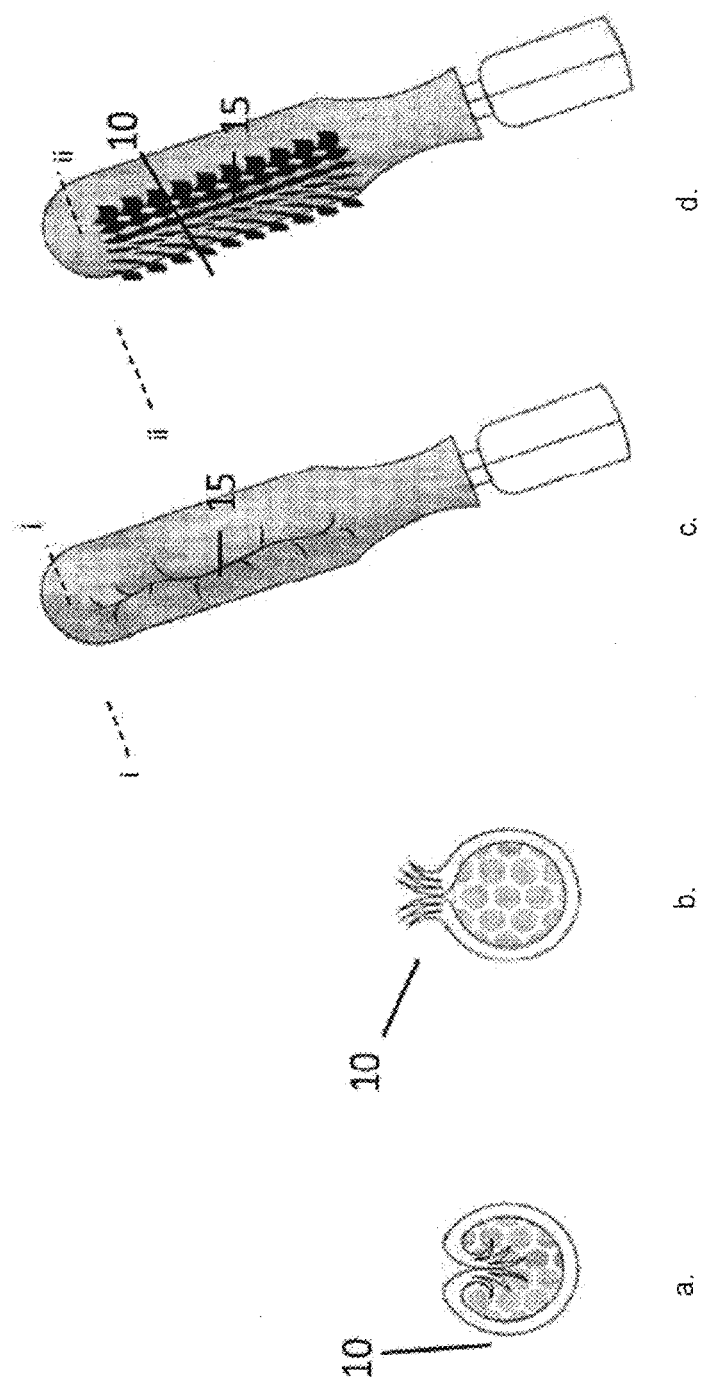
FIG. 15 depicts an inflatable brush head where the contact surface is only exposed upon inflation. (C) depicts an uninflated brush head with the contact surface unexposed and (D) depicts an inflated brush head with the contact surface exposed. (A) is a cross-sectional view of the uninflated brush head, taken along line i-i of (C). (B) is a cross-sectional view of the inflated brush head, taken along like ii-ii of (D).

In one embodiment, inflation of the bush head allows the opening up of a contact region for contacting the nasopharynx. For example, in the embodiment depicted in FIG. 15, in the uninflated form as shown in FIGS. 15(a) and (c), the surface 10 for contacting the nasopharynx is contained within the contact region 5. In the inflated form, as shown in FIGS. 15 (b) and (d), the surface for contacting the nasopharynx is on the exterior of the contact region 5.

Figure 16:
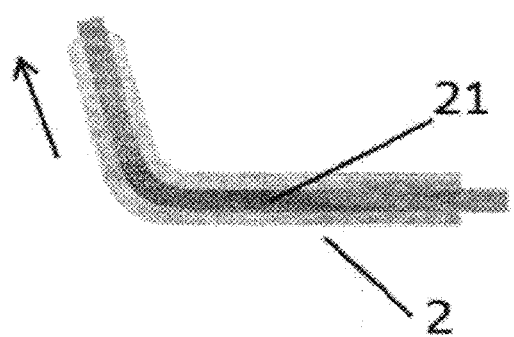
FIG. 16 depicts an air channel within the shaft of an inflatable brush head.

A person of skill in the art will readily appreciate that various means can be used for inflating the inflatable brush head. As shown in FIG. 16, the shaft 2 of the inflatable bush head optionally comprises an air channel 21 that allows air to enter the inflatable brush head (arrow points in the direction of the brush head).

Figure 17:
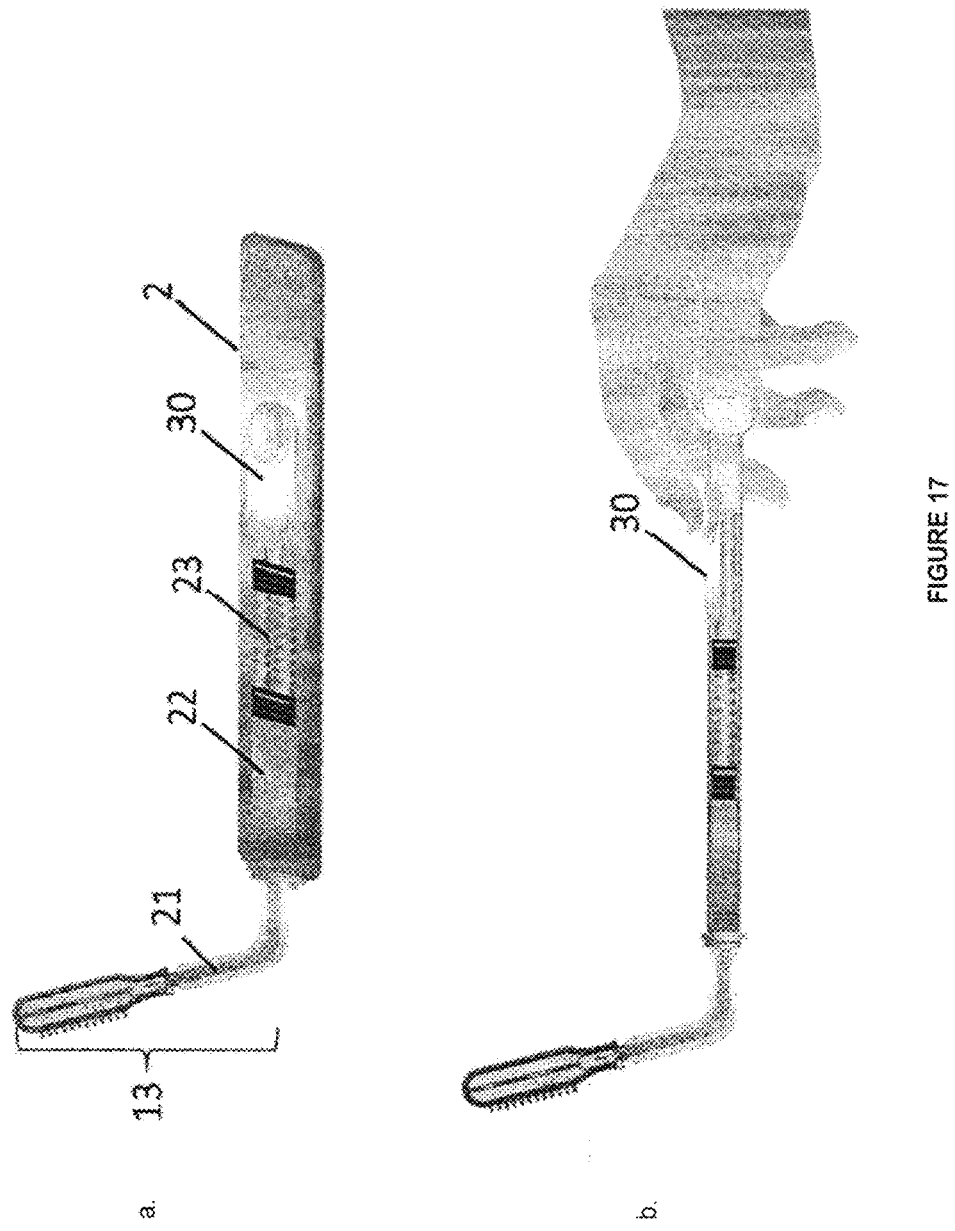
FIGS. 17(A) and (B) depicts an inflatable brush head including a means for inflating the brush head.
Figure 18:
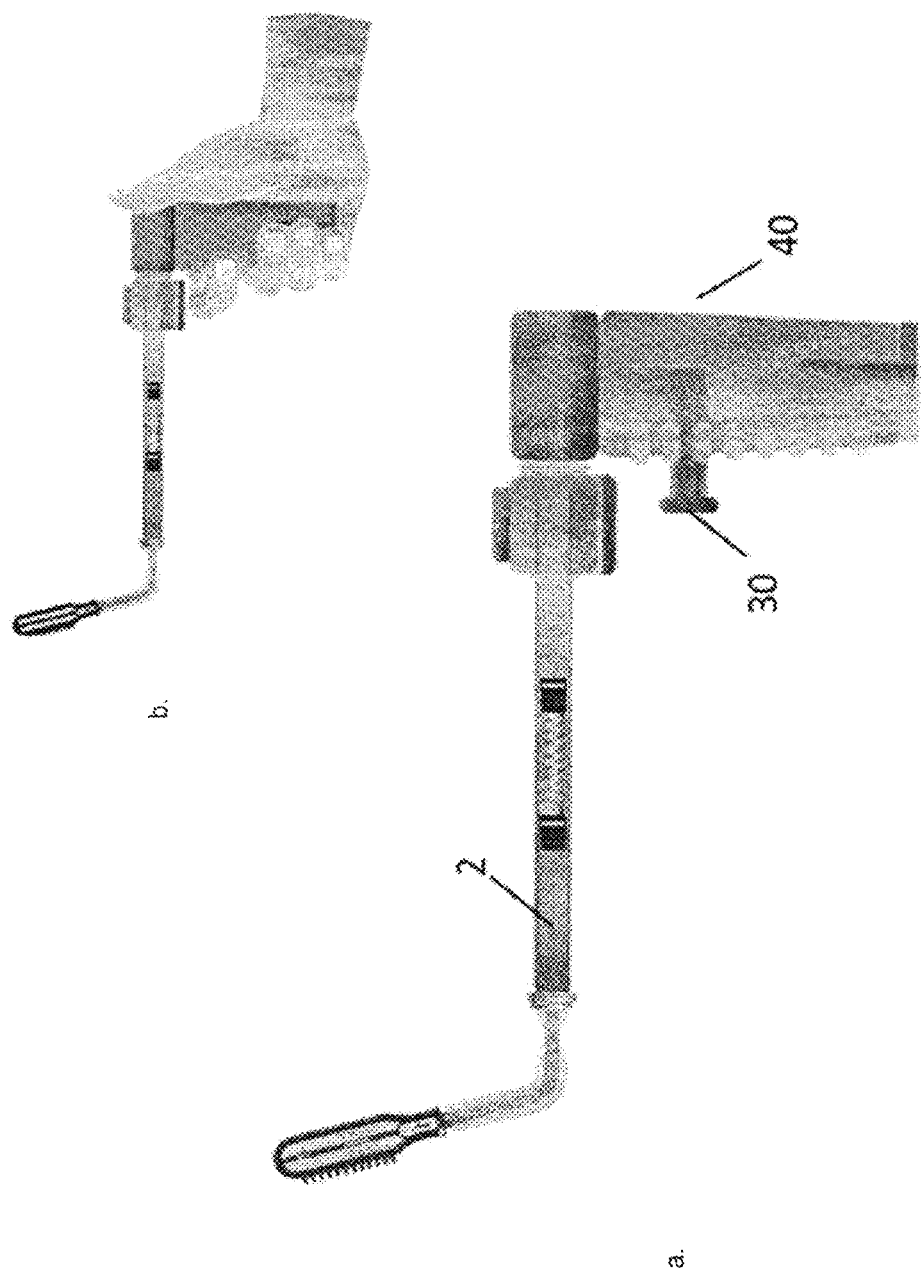
FIGS. 18(A) and (B) depicts an inflatable brush head connected to a handle containing a means for inflating the brush head.

Air can be introduced into the inflatable brush head through the air channel through various means. In one embodiment, the biopsy device includes a means for inflating the inflatable head. In one embodiment, the means for inflating the inflatable brush head comprises a hand operable trigger. The hand operable trigger 30 is optionally on the shaft 2 (FIGS. 17(a) and (b)) on a handle 40 extending from the shaft 2 (FIGS. 18(a) and (b)). In one embodiment, the handle 40 is detachable from the shaft 2. Movement of the hand operable trigger from a first position to a second position inflates the inflatable brush head. In one embodiment, the trigger is operably connected to a spring or coil 23 which is operably connected to the air channel 21, optionally through an air chamber 22. The spring or coil 23 is optionally located in the shaft 2. The air channel 21 leads to the inflatable brush head 13. Upon moving the trigger from the first position to the second position, the coil or spring is compressed which moves air into the air channel 2, optionally first through the air chamber 22, and into the inflatable brush head 13, thereby inflating it.

Other configurations of the inflatable brush biopsy device will be apparent to a person of skill in the art. For example, in a further embodiment, the device comprises two inflatable brush heads. The two inflatable brush heads are optionally configured in an analogous manner to the brush heads of the bifurcated brush head device described herein.

Brush with Light Handle

Another difficulty in obtaining biological samples from within the body relates to the visualization of the area to be sampled. For example, when taking a brush biopsy sample of the nasopharynx, the nasopharynx needs to be illuminated. Often this is accomplished with the dual use of both a light and a brushing device. However, such a system requires the operator to use both hands. The present inventors have developed a brush device for obtaining samples from a body surface such as the nasopharynx, where the device also includes a light. This device requires only one hand to both illuminate the body cavity and obtain the sample.

Accordingly, the bifurcated brush biopsy device and the inflatable brush devices described herein can also be used with a light handle. In one embodiment, the shaft of the device can be received in a handle comprising a light, optionally an LED light. The light is oriented such that it allows illumination of the area to be sampled. The handle optionally comprises a receptacle for receiving the shaft. Preferably, the receptacle portion has sufficient strength to support the blade to allow depression of the tongue. In a further embodiment, the handle further comprises a trigger for inflating the inflatable brush head. In one embodiment, the brush biopsy device is disposable while the light handle is reusable. The handle also optionally includes a means for inflating an inflatable brush head.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1: Nasopharyngeal Cancer Screening

Methods

A clinical trial was performed of a newly developed quantitative PCR NPC risk detection assay.

Screening and Detection of NPC was performed using the Trans-oral brush biopsy/Q-PCR EBV DNA detection system (NP Screen™) from Primex Laboratory, Van Nuys, Calif. The test kit includes a single use, trans-oral NP epithelial EBV DNA harvesting brush device mated with a DNA preservation solution and shipping vial.
Study Subjects, Sites and Design:
Inclusion Criteria:

Patients who underwent brush biopsy included confirmed NPC patients before treatment; high-risk Chinese individuals residing in Hong Kong or first-generation Chinese immigrants from high risk endemic areas residing in Toronto, Canada; those with family history of NPC; patients referred by primary physicians for routine ENT screening and/or ENT assessment due to the presence of clinical symptoms suspicious of NPC, or simply a patient's own request due to familial risk factors.
Exclusion Criteria:

Patients who were post-treatment for NPC; patients less than 20 years of age; immunosuppressed individuals; or patients who failed to adhere to the study follow-up assessment period of two years were excluded.

A total of 600 study subjects from two countries (Hong Kong, China: Radiation Oncology Clinic, Queen Mary Hospital, University of Hong Kong; Radiation Oncology Clinic and the Head and Neck Clinic, Queen Elizabeth Hospital. Toronto, Canada: Otolaryngology-Head and Neck Clinic, Rouge Valley Health System, Centenary Site, Scarborough, and two large ENT practices in Toronto). All probands had thorough clinical ENT/Head and Neck examinations by experienced ENT surgeons/or Oncologists with longstanding expertise in NPC diagnostics, followed by trans-nasal examination of the nasopharynx using a flexible endoscope.
Trans-Oral Brushing Procedure:

All subjects underwent trans-oral brushing of the NP with the device according to the manufacturer instructions. With the patient positioned upright and oral cavity exposed using a tongue depressor, the trans-oral brush is directed toward the posterior pharyngeal area. With the angled tip gently placed against the NP wall, gentle brushing and rotation is performed for the acquisition of NP epithelial samples (FIG. 1A).
Preservation, Preparation and Shipping of Samples:

After the brush is withdrawn from the oral cavity, the brush tip is detached from the brush handle and inserted into the shipping vial, where the specimen is immersed in the DNA preservation/shipping buffer as instructed by the manufacturer. Samples were identified by a bar-coded ID number, stored locally at room temperature and shipped to the assay laboratory in batches within 5 days.
Npc Diagnosis:
Npc Negative:

Subjects with normal ENT examinations, including normal nasopharyngoscopy were classified as NPC negative if they remained clinically and endoscopically negative for two years. Patients who underwent biopsy and had final histopathological diagnoses other than NPC were classified as NPC negative.
NPC Positive:

Only subjects with a suspicious NP lesion detected by endoscopy were biopsied according to standard of practice. Those with positive histopathology were classified as NPC positive.

Subjects classified as non-NPC by endoscopy, but with initial EBV-positive brushing results had re-brushing done at three to four months and regular follow-up visits for up to two years. If these subjects remained clinically and/or endoscopically negative at 2 year follow-up, then the initial and/or re-brush positive results were considered false positive (FP). In addition, subjects with positive EBV brushings but negative biopsy were also classified as brush FP.

Subjects with equivocal results had re-brushing in three months and follow-up visits up to two years with ENT and endoscopic examination of the NP.
Sample Processing and Quantitative Polymerase Chain Reaction DNA (Q-PCR) Analyses:

Samples were processed by Primex Laboratory using the ABI Prism 7700 sequence detection system (Applied Biosystems (ABI), Fostercity, Calif.). DNA from brushed samples was extracted using the Qiagen automated DNA extraction robot model 9604 (Valencia, Calif.). DNA was measured by fluorometry and adjusted to 10 ng/µL. Taqman 96 well plates were seeded with 42 duplicate brushing samples (5 µL), and replicate standards (5000, 500, 50, 5 and 0 EBV copies). The Taqman Universal PCR Master Mix, Uracyl N Glycosylase and internal standard primer/probes sets for the human genomic Small Ribosomal Sub-unit locus were purchased from ABI.

Q-PCR and Determination of Epstein Barr Virus DNA Load (Epstein-Barr virus Detection Levels-EDL):

The test involves in vitro nucleic acid hybridization using real time polymerase chain reaction (Q-PCR) for the detection, amplification and quantitation of Epstein-Barr virus (EBV) DNA. The test amplifies specific regions of the EBV genome and is detected via florescent dyes. These dyes are oligonucleotide probes, which bind specifically to the amplified products. EBV-EBNA-1 primers/probes (5'-3') providing the highest sensitivity and specificity in correlating with NPC diagnosis as determined by Primex Laboratory were used. Monitoring the fluorescence intensities during the PCR run allows the detection and quantitation of the accumulating products. The output is the fractional number of cycles (Ct) to achieve a predetermined intensity level, which is then converted to Epstein Barr Virus DNA Detection Level (EDL) using the established standard curve. Following un-blinding of bar codes, they were matched with clinical data.

Q-PCR analyses were also performed on 32 of the histologically confirmed solid biopsy NPC tumor specimens and compared with 20 histologically negative solid specimens. The distribution patterns of the EDL from the solid tumors were then compared with the EDL distribution curve of those from trans-oral brush biopsy.

EDL Results Reporting and Interpretations:

According to the laboratory reference guide, results of the NPScreen™ were classified as Normal/Negative (EDL of less than 1.7); Equivocal (EDL of 1.7 to 2.6); Abnormal/Positive (EDL of equal or greater than 2.7).

Statistics:

Numeric values were analyzed by Mann-Whitney tests. Cohorts were compared by Fisher's exact test. Woolf's approximation was used to calculate odds ratio. All tests were two-tailed and significance was set at 5%.

Results

Trans-Oral Brushings

A total of 600 patients analyzed had trans-oral brushings using the NPScreen™. The process is generally completed within one minute and all but two patients, tolerated the procedure well. There were no adverse events recorded including bleeding, excessive pain, nausea or vomiting. All patients were discharged from the clinics without complications. Two patients had hyperactive gag reflex and unable to tolerate the procedure. These two patients did not report any adverse events prior to discharge. A total of 11 patients had incomplete brushings, leading to insufficient DNA results. Ten of the insufficient samples were collected during the early part of the study period (during the first 100 patients). Subsequently, all remaining brushings were successful with only one failure. Reasons for insufficient DNA were reported as due to brusher's initial lack of experience and/or inability to access the nasopharynx; or insufficient brushing pressure applied to retrieve enough superficial epithelial cell layers for sampling.

Figure 2:
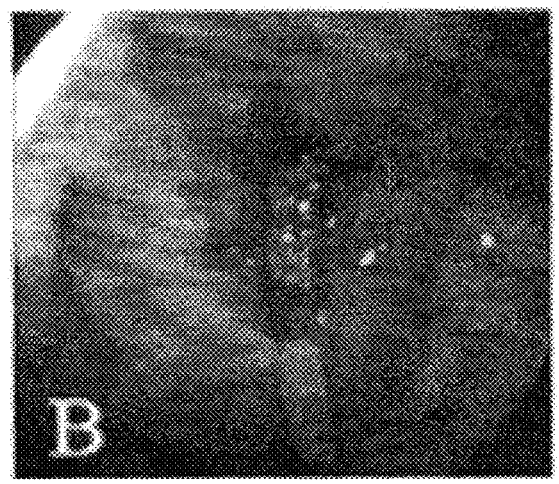
FIG. 2(A) shows an endoscopic image depicting the positioning of the brush tip at the retronasal wall.
FIG. 2(B) shows an endoscopic image of the post-brushing mucosal surface showing minimal maceration bleeding.
Figure 2:
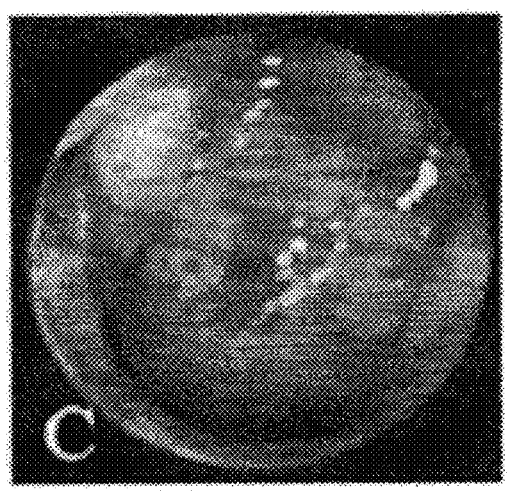

The trans-oral brushing seems to provide adequate access to both sides of the fossae of the Rosenmueller of the NP. This was confirmed by several concurrent endoscopic guided photographs, localizing the brush on both sides of the NP space. Post-brushing endoscopy further demonstrated minimal maceration of the epithelial surface with negligible, if any, bleeding (FIGS. 1B, 2A, 2B). Thus, the tissue harvest by the brushing tip appears to be mostly superficial.

Figure 3:
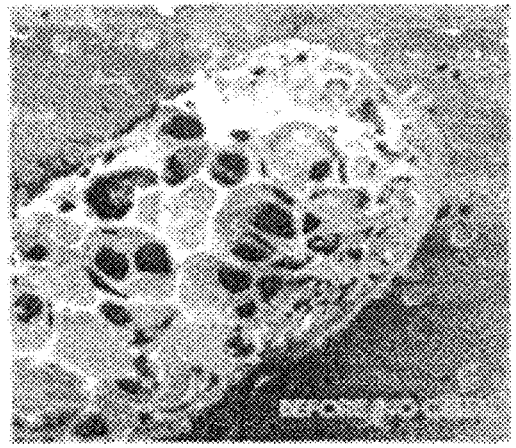
FIG. 3 shows various electron microscope images. (A) shows an unused trans-oral brush tip. (B) shows low magnification of brush tip with trapped NP tissue. (C) shows intermediate magnification (150×) of mostly intact harvested NP epithelium cells. (D) shows higher magnification (600×) of NP tissue harvest with intact epithelial cell layer with cell cohesion.
Figure 3:
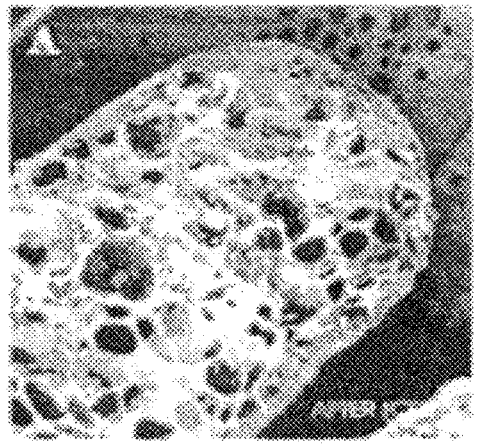
Figure 3:
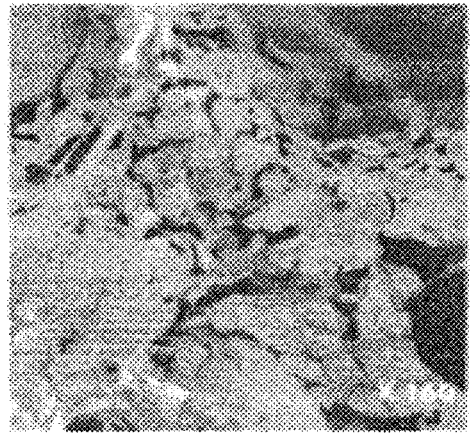
Figure 3:
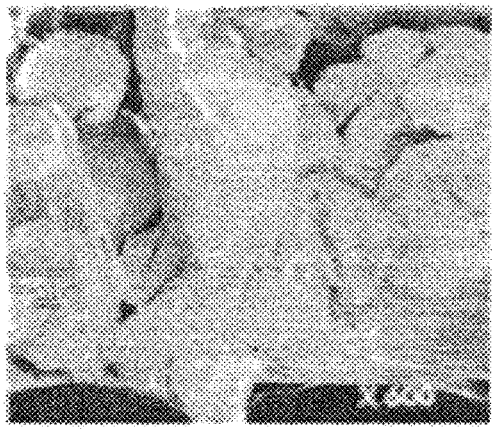

Nasopharyngeal epithelial tissue was shown to be trapped in the porous brush surface by scanning electron microscopy of the plastic brush surface before (FIG. 3A) and after tissue harvest (FIG. 3B,3C). Importantly, epithelial cells maintain cohesion (FIG. 3D) with little tissue destruction, suggesting predominately intact epithelium was harvested.

Sample Analysis:

Of the initial 600 patients, the final cohort was 578. This was after excluding the 13 samples with insufficient DNA (11 failed samples due to brusher inexperience and two incomplete brushings due to excessive patient gagging). Eight patients were unable to adhere to the two year follow-up assessment and were also excluded from the study. One patient with persistent equivocal findings without clinical evidence of disease was also excluded. The study demographics were comprised of 263 females (mean age: 53; range 28-82) and 315 males (mean age: 52; range: 20-86).

EDL Distributions for Solid NPC Tumor and Brush Biopsy Samples

Figure 4:
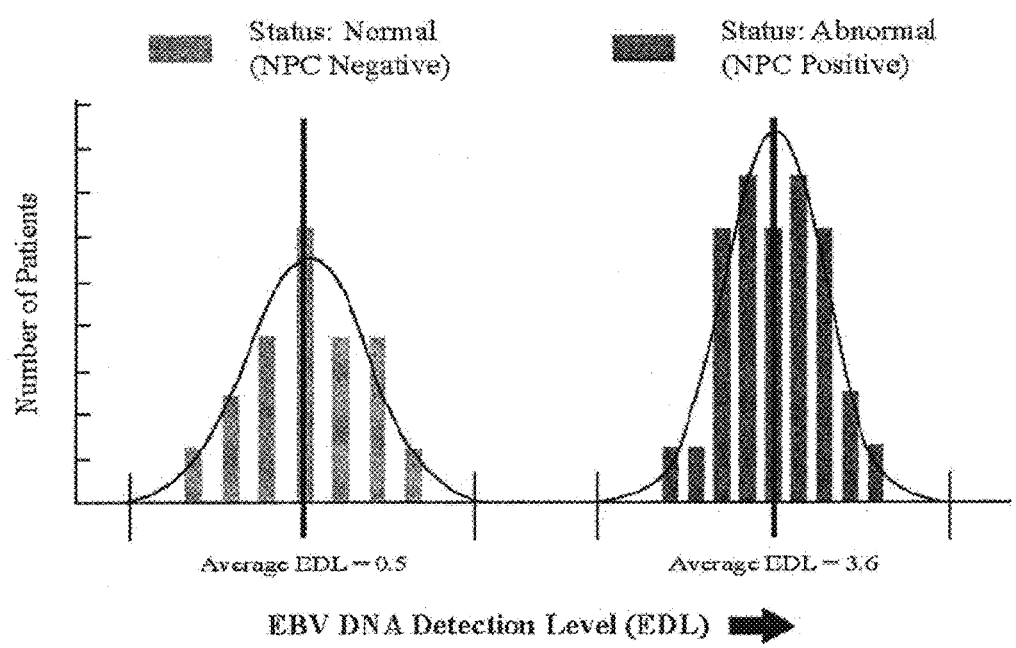
FIG. 4 shows the distribution patterns of EDL values for solid NPC tumor and normal subjects. The significant margin evident between the two histopathological types demonstrates the potential for this assay to discriminate patients without NPC molecular markers from those with NPC molecular markers.
Figure 5:
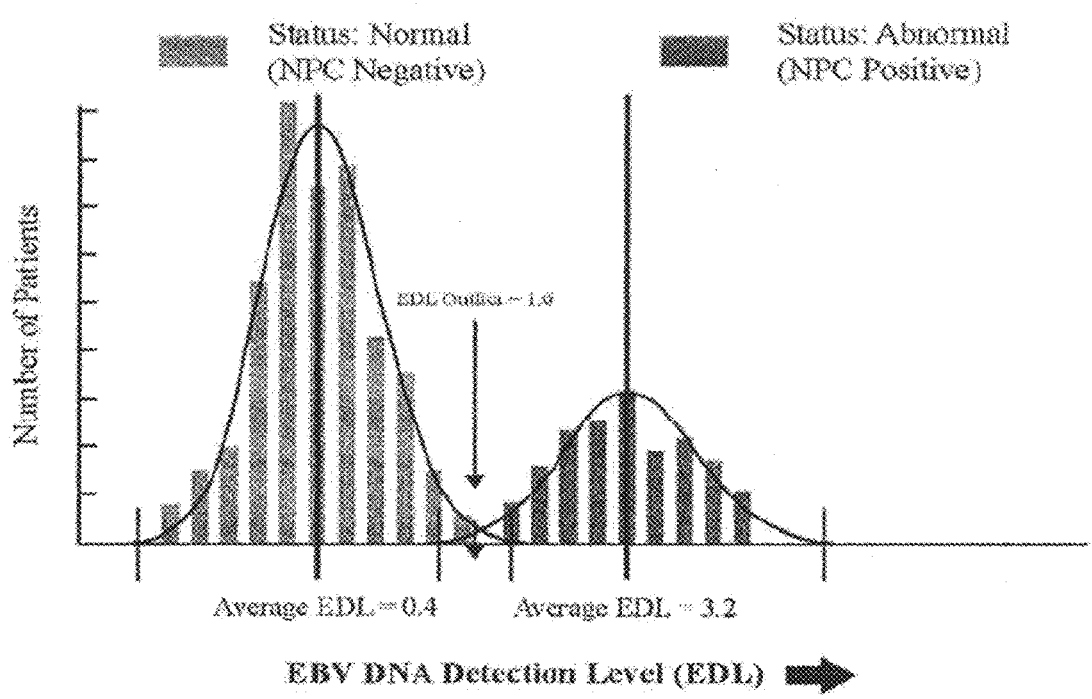
FIG. 5 shows the distribution patterns of EDL values for brushed NPC tumor and normal subjects. The two groups were clearly delineated by separate curves other than the one false negative result.

When analyzing and comparing EDL values from solid NPC tissues versus histopathological negative NP tissues, there was no overlap in the EDL values between these two groups (FIG. 4). Similarly, the EDL distribution of the brush biopsy results were clearly delineated by separate curves other than the one false negative outlier with an EDL of 1.6 (FIG. 5). This outlying patient had positive endoscopic findings and positive histology.

Initially there were 12 false positive brushings. Of these 12 false positives one patient was endoscopically positive but subsequent biopsy was negative. This patient had an EDL, which was just above the equivocal range. One patient had negative endoscopy and subsequent biopsy of the nasopharynx was histologically negative.

Of the 12 false positive brushings, 11 were endoscopically negative. Three (3/11) of these patients eventually presented clinically with histologically confirmed NPC, six (6/11) resolved to normal on retesting, one (1/11) patient without biopsy confirmation maintained his elevated EBV status on retest with no other clinical evidence of NPC in two years. This, therefore, resulted in a final total of 3 false positive brush results.

Initially 13 patients had equivocal results on brushing. Five (5/13) re-brushings were done and four (4/5) of these patients returned to normal on re-brushing. One (1/5) remained equivocal on re-brushing and is being monitored. Eight (8/13) patients did not get re-brushed and were lost to follow-up.

The brushing and assay performance on 578 patients yielded a sensitivity of 98.9% and specificity of 99.3% with positive predictive value of 96.9% and negative predictive value of 99.7%% (Table 1).

With respect to endoscopy, there were 131 cases with some form of abnormal or suspicious endoscopic findings, and biopsies were performed on 101 patients. All clinicians were highly experienced with respect to performing diagnostic endoscopy for NPC. Despite this, there were 14 false positive endoscopies leading to negative biopsies yielding a false positive rate of 13.8% (14/101). All 14 of the endoscopy false positives (NPC biopsy negative subjects) had no EBV DNA detected using the brushing method. There were also 5 false negative endoscopies in patients histologically found to have NPC and notably also had positive brushings. Table 2 demonstrates the results for nasoendoscopy.

Tumor staging was available in 67 of the histologically positive NPC patients. The brushings were found to confirm 15 T1 and 31 T2 lesions. The results comparing nasoendoscopy and brush biopsy are illustrated in Table 3. All patients from the endoscopy false negative group had positive EDL brushing results.

TABLE 1

Screening by nasoendoscopy yielded 14 false positive results and 5 false negative finding resulting in sensitivity of 94% and specificity of 97.1%.

| TP | TN | SENSITIVITY | PPV |
|---|---|---|---|
| 82 | 477 | 94% | 85% |
| FP | FN | SPECIFICITY | NPV |
| 14 | 5 | 97.1% | 98.9% |

TABLE 2

Screening by brushing method yielded 3 false positive results and 1 false negative finding resulting in sensitivity of 98.9% and specificity of 99.3%.

| TP | TN | SENSITIVITY | PPV |
|---|---|---|---|
| 94 | 480 | 98.9% [95% CI \| 92.8-100%] | 96.9% |
| FP | FN | SPECIFICITY | NPV |
| 3 | 1 | 99.3% [95% CI \| 97.8-100%] | 99.7% |

TABLE 3

Tumor staging was available for 67 histological NPC positive patients. Brush biopsy was able to diagnose early stage disease and was at least as comparable to nasoendoscopy.

| | NASO-ENDOSCOPY | | BRUSH BIOPSY | |
|---|---|---|---|---|
| | TP | FN | TP | FN |
| T1 | 12 | 3 | T1 15 | 0 |
| T2 | 32 | 0 | T2 31 | 1 |
| T3 | 9 | 1 | T3 10 | 0 |
| T4 | 10 | 0 | T4 10 | 0 |

Discussion

Nasopharyngeal Carcinoma is a common head and neck cancer in Southern China, one of the most densely populated regions of the world and is the endemic high risk area for this disease (Wei and Sham). Due to the large Chinese immigrant population worldwide including the US, Canada and Europe, there is a significant global population at risk (Ferlay et al, Jia et al, Cao et al). Because of the obscure anatomical location and the lack of early signs or symptoms, the majority of NPC cases are diagnosed late with poor prognosis and survival despite significant advances in radiation and chemotherapy. Unfortunately, there is still a paucity of highly sensitive and efficient tools available to provide large-scale population screening of this disease. Besides nasoendoscopy, EBV serology and plasma EBV DNA are the current available detection methods (Lo et al 1999a, Lo et al 1999b, Lo et al 2000, Tsang et al, Cheng et al). However, over 90% of adult individuals have prior exposure to EBV infection, rendering the serology a poor screening test alone (Maeda et al, Savard et al, Gulley et al, Macsween et al). Studies have shown improved sensitivity and specificity by combining serology with plasma EBV DNA testing (Teresa et al, Leung et al) However the plasma method relies on obtaining a sufficient quantity of plasma EBV DNA or its partially degraded segments for detection. DNA is exceedingly labile such that preservation of the plasma samples containing DNA can be challenging when there are multiple physicians sample collection sites, and the testing laboratory locations are remote. Moreover, the value of the plasma method in detecting early or small localized tumors is still unknown (Stevens et al, Le et al, Anker et al).

An ideal screening and detection test should be non-invasive, relatively inexpensive; simple to perform; have a high patient compliance potential; and be highly sensitive and specific for large-scale robust detection of disease. Using the aforementioned parameters as a guide, this study attempted to evaluate the newly developed ambulatory genetic-based NPC detection system and compare it with endoscopy, the current gold standard method of NPC detection.

From a clinician and otolaryngologist perspective, accessing and obtaining adequate sample from the NP conveniently and comfortably has always been a challenge. Previous published studies (Tune et al, Adham et al) have described a trans-nasal approach in obtaining NP tissues for EBV DNA analyses. This approach however can be complicated and hindered by anatomical obstructions within anterior nasal cavities such as septal deviation or turbinate hypertrophy. Patient's discomfort is a major obstacle in wide spread adoption of the trans-nasal method. Furthermore, bilateral brushing to cover both sides of NP via both nasal cavities adds to poor adoption and patient compliance. With the current trans-oral method, the process can be performed using a single entry via the oral cavity to access and sample both left and right fossae of Rosenmueller, an area where NPC commonly originate. This was clearly demonstrated and confirmed in several endoscopic views of the brush positions. During the early phase of this trial, 12 samples were found to have insufficient DNA for analysis. This failure is most likely attributable to brusher inexperience and/or difficulty in controlling/limiting patient gagging. It also appears that excessive brushing pressure is not necessary to obtain sufficient amount of epithelial samples, as most patients did not record excessive gag reaction from the brushing. After further brush training, the subsequent group of patients' records demonstrated only one case of insufficient DNA. Overall, the method was found to be safe; easy to adopt and learned, and could be performed by non-physicians such as nurse practitioners.

Direct access to the NP for cellular EBV DNA detection can have several major advantages. The samples obtained by brushing in this study, as demonstrated using electron microscopy, are predominately intact freshly sloughed, epithelial layers. Therefore, the EBV DNA measured should reflect the actual epithelial intracellular tumor DNA load, as opposed to measuring plasma EBV DNA or its fragments released from necrotic cells or through apoptosis (Mutirangura et al, Fournie et al). The trans-oral brushing seems to retrieve samples closely resembling those from traditional direct biopsy method as demonstrated in the nearly identical EBV EDL distribution patterns between the two methods. This method of rapid retrieval of samples paired with immediate DNA preservation may also permit precise quantitation of intact intracellular EBV DNA load with minimal degradation or changes. Direct biopsy and access to the primary tumor site may potentially be a much better and more sensitive way in detecting early disease when the tumor EBV DNA load is very small and not detectable in the plasma. For instance, an early-stage, pre-neoplastic NP lesion with negligible necrosis and cell death may not have enough EBV DNA in the blood yet still be detectable through superficial brush biopsy.

The current gold standard of clinical NPC detection is nasopharyngoscopy, combined with biopsy of suspicious lesions. There are considerable drawbacks to nasoendoscopy. NPC often spreads submucosally and endoscopic detection misses over half of early stages unless combined with multiple biopsies (Low et al, Sham et al). In this study, 5 NPC patients without endoscopic abnormality were detectable by the brushing method. One of the false negative endoscopy patients had T3 advanced metastatic neck disease despite minimal NP findings. Furthermore, there are many common conditions such as epistaxis and non-specific endoscopic NP findings that can mimic occult or early stage NPC. The skill dependency and subjectivity of endoscopy in combination with the inherent biases towards caution can lead to untoward patients' anxiety and unnecessary biopsy. In this study, 14% of the biopsy based on positive endoscopy did not lead to final diagnosis of NPC. In endemic regions with high case loads, nasopharyngoscopy presents an additional challenge, as endoscopes require expensive cleaning and autoclaving with long turnaround time, considerably reducing the number of subjects that can be screened per day, not to mention the additional patient comfort/anxiety due to the semi-invasive nature of trans-nasal procedure.

The results of this study confirm a high degree of sensitivity (98.9%) and specificity (99.3%) of using NPScreen™ in detection of NPC, comparable to and superior to some of the previous, research laboratory-based trans-nasal studies (Tune et al, Tong et al, Adham et al), as well as the published EBV serology or plasma EBV DNA results (Leung et al, Liu et al 2011, Liu et al 2012, Xang et al, Bortolin et al, Lin et al). However, the fact that this current method offers access and sampling of the NP directly for retrieval of EBV infected epithelial cells can be a significant advantage over other methods for early detection. This hypothesis is supported by the observations that several brush positive NPC cases were negative endoscopically, likely representing early sub-mucosal disease with minimal tumor volume. The brushing also helped to identify asymptomatic and endoscopically-negative patients with strong family history who were subsequently confirmed to have NPC by biopsy. A good proportion (46/67, 69%) of stage T1 and T2 of NPC were detected using the brush method. One of the patients with negative endoscopy and negative biopsy but positive brushing result developed positive endoscopy and histopathology one year after the initial brushing was performed. This finding suggests that the brushing method can have a lead-time as long as one year before the tumor is clinically apparent. The overall high sensitivity of superficial brush biopsies to harvest positive tumor cells remains a mystery given the sub mucosal spread of many NPC. The observations imply that NPC tumor cells may not necessarily stay contiguous with the tumor, but that they migrate with normal epithelium to be shed into the retro-nasal NP space. If correct, this would not only explain the efficiency of NPC detection in superficial brushing samples, but it would suggest that NPC tumors maintain core aspects of normal epithelial cell physiology.

In this study, there were two false positive brush results identified. One of the FP patients who had EDL just at the outside limit of equivocal range has persistent abnormal lymphoid-like tissues in the NP by endoscopy. Multi-quadrant deep biopsies by an experienced ENT surgeon failed to reveal any histologic abnormalities although a missed biopsy of a very small lesion could still be a distant possibility. Alternatively, this patient may have persistent EBV infection or EBV harboring lymphoid/epithelial tissues in the NP contributing to the false positive findings. Another patient with false positive brush results has a strong family history of NPC and has persistent elevated EDL value after re-brushing. The possibility that both patients harbor small occult or pre-neoplastic NPC cannot be completely excluded. Both patients are being monitored clinically with regular endoscopy.

In the current study, 13 patients had EDL values in the equivocal range. With respect to the clinical implications of equivocal EDL, it is possible that active and persistent EBV-infected epithelial tissues harboring EBV DNA contributes to the sources of positive findings. Upon re-brushing after three months, 4 patients reverted back to normal brush results, suggesting that resolution of the acute infectious process can lead to resolution of positive brush results. The 1 patient with persistent equivocal EDL may harbor occult carcinoma or have persistent EBV infected lymphoid or epithelial cells in the brushed areas. Therefore, patients with acute upper respiratory tract infection or related symptoms should avoid brushing until the acute symptoms are resolved. The remaining 8 patients' clinical and EDL status cannot be ascertained as they were lost to follow-up within the two years' study time frame. Under normal clinical settings, patients with equivocal EDL probably should be monitored with endoscopy and re-brushed at regular intervals.

The biological relationship between the degree of EBV DNA positivity (number of EBV genome copy equivalents) and clinical status or treatment outcome is not entirely known. It has been demonstrated in numerous studies that pre-treatment and post radiotherapy plasma EBV DNA levels have prognostic values in predicting treatment outcomes, including recurrence and metastases (Lo et al 1999a, Lin et al, Gulley et al, Lo et al, Chan et al, Leon et al, Usudel et al, Shao et al, Anker et al). Given the fact that the brushing method accesses the NP directly and harvests fresh NPC tumor cells, this method can potentially be another way to determine the actual intracellular EBV DNA load.

In summary, in testing the utility of this new NPC detection kit by collecting retronasal NP brushing samples in several ambulatory clinic/practice sites in Hong Kong and Canada, the study demonstrated that the new trans-oral brushing methodology provides clinically useful DNA for detection of tissue-borne EBV DNA. This non-invasive procedure was well tolerated, and easily learned by trained physicians. It can be rapidly performed in ambulatory settings, where it compared well with the more expensive, time-consuming subjective nasopharyngoscopy. This system is based on a high throughput real-time genomic quantitative PCR. Collectively, the present study validates the trans-oral brushing system as a good candidate for large population sensitive and specific screening of NPC. Prospective, population-based studies of subjects undergoing trans-oral brushing procedures at regular intervals are needed to determine if it can consistently detect early disease and change the demography and prognosis of NPC.

Example 2: Screening Assay for NPC

The assay described below provides information about the EBV DNA status in specimen derived from the posterior nasopharynx of a high-risk for NPC patient. The assay result is compared to a reference standard to determine a patient's contemporary risk for NPC.
Overview of Assay:
1) Specimen Collection
  Specimen is collected using a trans-oral nasopharyngeal brush.
2) Specimen Transport
  Specimen is secured and transported to the laboratory using the transport media.

3) DNA Release and Extraction

Total DNA is isolated from the specimen using the Roche MagNA Nucleic Acid Isolation Station and the MagNA Pure LC DNA Isolation Kit.

4) DNA Quantitation

Total DNA is quantitated using fluorometric DNA-binding dye, PicoGreen® dsDNA Quantitation Kit, Molecular Probes, P-7589, in combination with fluorometry, Fluoroskan Ascent Fla., Thermo Labsystems, 5210460, and then total DNA is normalized to 10 ng/plI concentration.

5) Real Time PCR

Template consists of 50 ng (=5 µl of ~10 ng/µl) total DNA. EBNA1 and human RNaseP target sequences are detected and co amplified using primers and TaqMan® probes on an ABI Prism® 7000 SDS platform. EBNA1 is the clinically relevant analyte while the RNaseP analyte serves as the quantitated internal amplification control as well as the quantitated assay method control. EBV DNA reference material is used as a quantitated external control. The real-time PCR threshold cycle number, Ct (FAM) for EBNA1 detection and Ct (VIC) for RNaseP detection, are the output results.

6) Acceptance of Real-Time PCR Results (a) Batch Specific Controls: The real-time PCR run is accepted if controls perform as expected and are within specified upper and lower limits otherwise the batch is rejected.

(b) Sample Specific Controls: Each test result of each patient is accepted as valid controls perform as expected and are within upper and lower limits otherwise the result is not reported.

7) NPC Risk Assessment (Clinical)

EBNA1 detection results, Ct(FAM)>31.50, correlate to low clinical risk for NPC.

Specimen Collection:

A trans-oral nasopharyngeal brush is used to collect a sample from the posterior nasopharynx. After collection, the nasopharyngeal specimen is secured in a 2 ml plastic screw-cap tube containing 500 µl of the transport buffer described below.

Transport Buffer:

The transport buffer is a hypertonic maintenance media used to minimize nucleic acid degradation.

DNA Release Isolation and Normalization to 10 ng/µl Concentration:

At the laboratory the 2 ml transport tube is vortexed for 60 seconds and 200 µl of the suspension is drawn off for DNA extraction. Total DNA (DNA) is released and isolated from the suspension using the MagNA Nucleic Acid Isolation Station and the MagNA Pure LC DNA Isolation Kit, Code: 03003990001 (Roche Diagnostics, IN). The DNA isolate is quantitated using fluorometric DNAbinding dye (PicoGreen® dsDNA Quantitation Kit, Molecular Probes, P-7589), in combination with fluorometery (Fluoroskan Ascent Fla., Thermo Labsystems, 5210460) then the DNA is normalized to 10 ng/µl concentration using molecular grade water. For real-time PCR analysis duplicate 5 µl aliquots are used, therefore at least 115 ng of DNA (=2□~5 µl□~10 ng/µl plus 15% for residual loss in tips etc.) must be available for testing otherwise the DNA extraction protocol is repeated or, in the case of insufficient extractable DNA from the native specimen, the patient must be rebrushed.

Primer/Probe Targets:

Target sequences located in the EBV EBNA1 gene and the human RNaseP gene are detected and co amplified during the PCR reaction. For patient samples EBNA1 is the clinically relevant analyte while RNaseP, serves as the quantitated internal control as well as the assay quantitated method control.

EBV Primers/TaqMan® Probe:

Real-time PCR primers and Taqman® probe (primer and probe) were developed from the prototypic EBV B95.8 genome sequence downloaded from GenBank, Accession No. V01555, length=172,281 bp. Primers amplify a 75 bp (Gaps=0/75) fragment located in the EBNA1 gene, nucleotide numbers, 109,559 to 109,633. The TaqMan® probe is a sequence specific dually fluorophore-labeled DNA oligonucleotide conjugate (fluorogenic probe). One fluorophore is termed the reporter (5'-end) and the other is the quencher (3'-end). The TaqMan® probe, length=20 bp, is specific to a region located between the forward and reverse primers. The reporter and quencher fluorophores associated with the EBNA1 probe are FAM and TAMRA respectively. Primers and TaqMan® probe are synthesized by Applied Biosystems, Foster City, Calif. and are internally validated prior to use.

EBV Amplicon (B95.8 genome nucleotides: 109,559 to 109,633):
(sequences corresponding to the primers listed below are underlined)
[SEQ ID NO: 3]
GTCGTCTCCCCTTTGGAATGGCCCCTGGACCCGGCCCACAACCTGGC
CCGCTAAGGAGTCCATTGTCTGTTATT Forward Primer:
[SEQ ID NO: 1]
5'-GTC GTC TCC CCT TTG GAA TG-3'

Reverse Primer:
[SEQ ID NO: 2]
5'-AAT AAC AGA CAA TGG ACT CCC TTA GC-3'

TaqMan ® Probe:
[SEQ ID NO: 4]
5'-(FAM) CCT GGA CCC GGC CCA CAA CC (TAMRA)-3'

RNaseP Primers/TaqMan® Probe:

Real-time PCR primers and TaqMan® probe against the human RNaseP gene, which exists as a single copy per haploid genome, serves as the quantitated internal amplification control as well as the quantitation method control. The TaqMan® RNaseP Detection Reagent Kit, 4316831 (RNP) (Applied Biosystems, Foster City, Calif.) is used to amplify and detect the RNaseP gene target sequence. The reporter and quencher fluorophores associated with the RNaseP gene probe are VIC and TAMRA respectively.

Real-Time PCR Technology:

Real-time PCR chemistry is performed on a ABI Prism® 7000 SDS platform (Applied Biosystems, Foster City, Calif.). During PCR the forward and reverse primers define the endpoints of the amplicon and provide the first level of analytical specificity for the assay. The second level of analytical specificity is provided by the fluorogenic probe, which hybridizes to a specific complimentary region between the forward and reverse primers during the annealing/extension phase of the PCR reaction. The fluorogenic probe is labeled with a reporter fluorophore at the 5'-end and a quencher fluorophore at the 3'-end and as long as the reporter and quencher fluorophores remain in close proximity the emission spectrum of the reporter is quenched. During real-time PCR, if the target amplicon is present, the probe hybridizes to the amplicon and during the 5'-exonuclease activity of the taq polymerase the probe is broken apart liberating the reporter to emit a measurable fluorescent signal. The fluorescence signal is recorded during the PCR cycle and is proportional to the amount of amplicon product amplified to that point in the reaction. The more target sequences present in the starter template, the fewer PCR cycles it will take the fluorescence to accrue to a point where the signal is detected by the instrument. The cycle at which the fluorescence signal is first recorded as statistically significant above back-ground is defined as the threshold cycle number, Ct, and is the reported result for the assay. Several nucleic acid targets may be coamplified and their respective Ct values are differentiated by the unique emission of their reporter fluorophores, i.e Ct (FAM) for the TaqMan® probe targeting the EBNA1 gene and, Ct(VIC) for the probe targeting the RNaseP gene.

Figure 6:
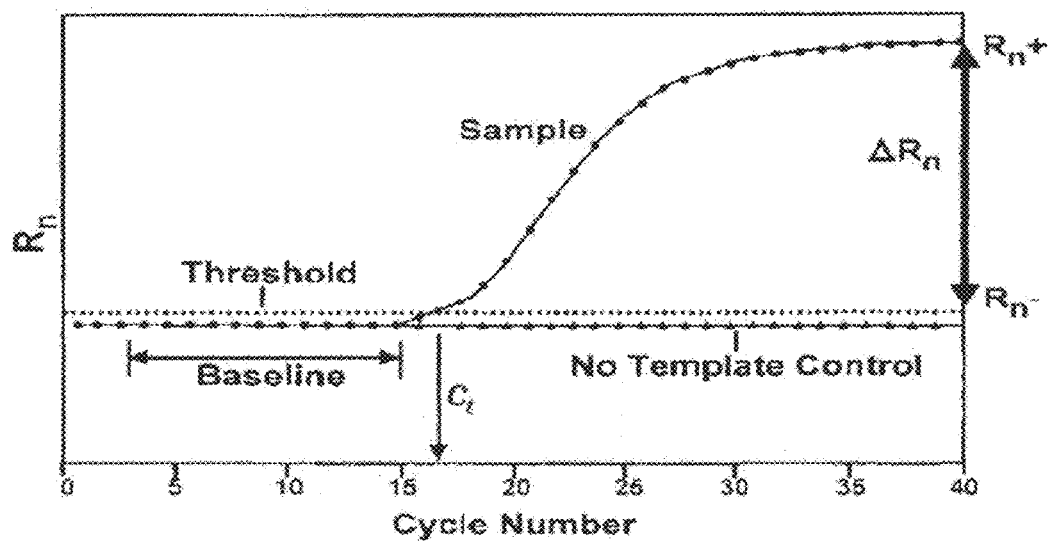
FIG. 6 shows the four major phases in real-time PCR; the linear ground phase, the early exponential phase, the log-linear phase, and plateau phase.
Figure 7A:
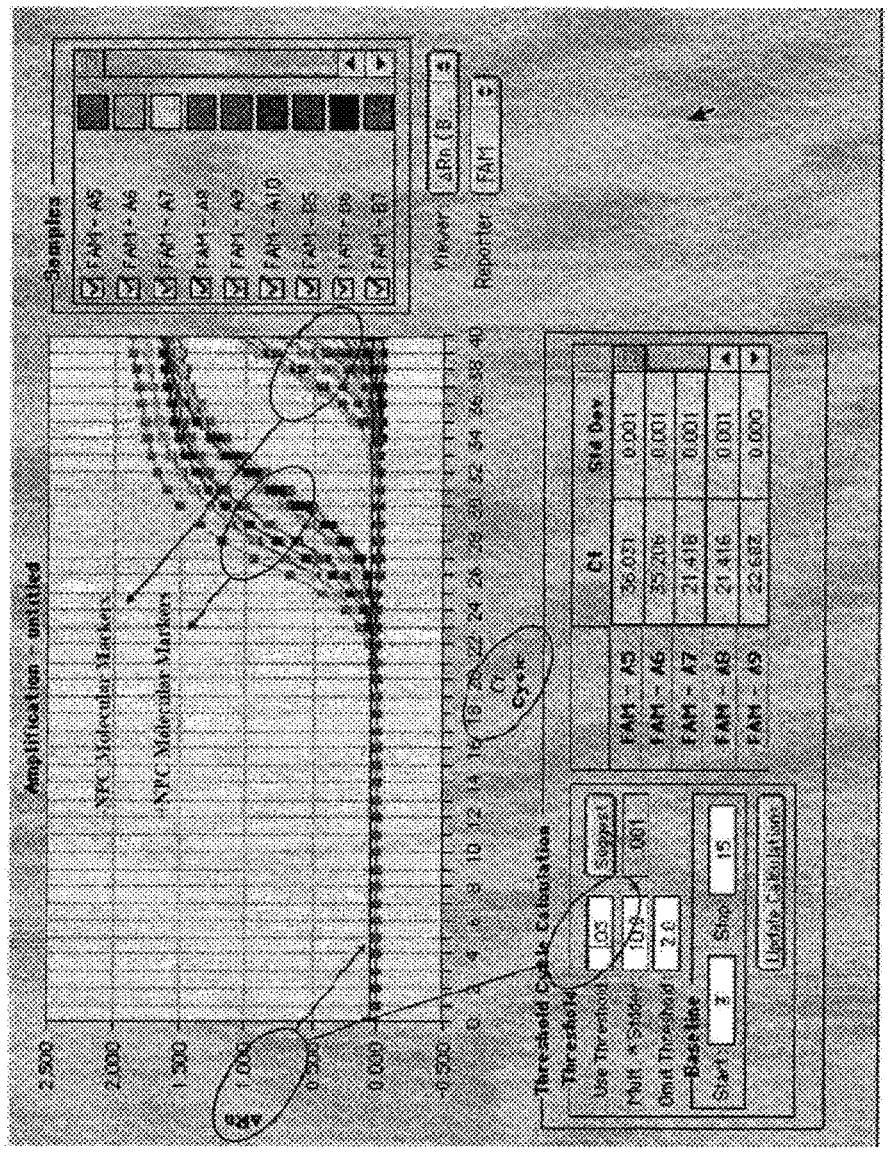
FIG. 7(A) shows a typical amplification curve for ABI Prism® SDS.

As shown in FIG. 6, there are four major phases in real-time PCR; the linear ground phase, the early exponential phase, the log-linear phase, and plateau phase. During the linear ground phase, Ct<15, PCR is just beginning, and fluorescence emission at each cycle are not greater than the background. At the early exponential phase, the amount of fluorescence reaches the threshold where it is significantly higher than background levels. The crossing point or cycle at which this occurs is the Ct. The more target sequences present in the starter template, the fewer PCR cycles it will take the fluorescence intensity to cross the threshold. As shown in FIG. 7(A), Ct(FAM) values for EBV DNA detection in samples derived from normal patients are typified by, FAM-A5=36.031 and FAM-A6=35.206 while values for samples derived from NPC positive patients are typified by Ct(FAM) values; FAM-A7=21.418, FAM-A8=21.416 and FAM-A9=22.683.

PCR Setup and Run Specifications for the Assay:

PCR reaction setup is detailed in Table 4 and amplification conditions are detailed in Table 5 and Table 6. Uracyl N Glycosylase is included in each reaction to prevent contamination. To check for contamination, each run includes two no-template controls (NTC) in which nuclease-free H2O is substituted for template. Three replicates each from two concentrations of EBV DNA reference material at 9.3 fg (=5 μl×1.85 fg/μl) and 92.5 fg (=5 μl×18.50 fg/μl) serve as the quantitated external control. The human RNaseP gene (which exists as a single copy per haploid genome) serves as a quantitated internal control to monitor for inhibition of the PCR reaction and because the quantitation is known, i.e. approx. 15,000 copies (=50 ng/3.30 pg), it also serves as the method control.

TABLE 4

Real time PCR setup.

| Component | Each | Final Concentration |
|---|---|---|
| Patient DNA (10 ng/μl) | 5.0 | 2 ng/μl |
| Taqman Master Mix, 2X | 12.5 | 1X |
| EBV EBNA1 Forward Primer (10 uM) | 0.5 | 200 nM |
| EBV EBNA1 Reverse Primer (10 uM) | 0.5 | 200 nM |
| EBV EBNA1 FAM Probe (10 uM) | 0.25 | 100 nM |
| RNase P F&R Primers, VIC Probe(10 uM) | 1.25 | 200/200/100 nM |
| Molecular Grade H₂O | 5.00 | |
| Total (25.0 μl) | 25.0 μl | |

TABLE 5

Thermocycle Conditions (ABI Prism ® SDS)

| Stage | Cycle Reps | Temperature | Duration |
|---|---|---|---|
| Stage 1 | 1 | 50 | 2 Min |
| Stage 2 | 2 | 95 | 10 Min |
| Stage 3 | 40 | 91 | 15 Sec |
| | — | 60 | 1 Min |

TABLE 6

Base Line Settings (ABI Prism ® SDS)

| Detector | FAM (EBV) | VIC (RNP) |
|---|---|---|
| Baseline Threshold | 0.05 | 0.25 |
| Baseline Start (cycle) | 1 | 1 |
| Baseline End (cycle) | 15 | 15 |

96 Well Plate Sample Mapping:

For a maximum of 44 samples: pipette 5 μl of sample concentration into wells A2 to D7 (F01 to F44 inclusive), then pipette a duplicate 5 μl of sample concentration into wells E7 to H12 (S01 to S44 inclusive) and log the association between the duplicates, i.e Fn, n=1, 2, 3 . . . 44, is associated with Sn, n=1, 2, 3 . . . 44. See Table 7 below for details.

Pipette 5 μl of ddH2O into wells G1 and H1 for the No Template Control (NTC).

Pipette 3 replicates of 5 μl at 10 copies/μl, EBV DNA control in wells A1, B1 and C1.

Pipette 3 replicates of 5 μl at 100 copies/μl, EBV DNA control in wells D1, E1 and F1.

TABLE 7

Sample mapping for 96-well optical reaction plate

| | 1 | 2 | 3 | 4 | 5 | 6 | 7 | 8 | 9 | 10 | 11 | 12 |
|---|---|---|---|---|---|---|---|---|---|---|---|---|
| A | L01 | F01 | F09 | F17 | F25 | F33 | F41 | S05 | S13 | S21 | S29 | S37 |
| B | L02 | F02 | F10 | F18 | F26 | F34 | F42 | S06 | S14 | S22 | S30 | S38 |
| C | L03 | F03 | F11 | F19 | F27 | F35 | F43 | S07 | S15 | S23 | S31 | S39 |
| D | DO1 | F04 | F12 | F20 | F28 | F36 | F44 | S08 | S16 | S24 | S32 | S40 |
| E | DO2 | F05 | F13 | F21 | F29 | F37 | S01 | S09 | S17 | S25 | S33 | S41 |
| F | DO3 | F06 | F14 | F22 | F30 | F38 | S02 | S10 | S18 | S26 | S34 | S42 |
| G | NTC | F07 | F15 | F23 | F31 | F39 | S03 | S11 | S19 | S27 | S35 | S43 |
| H | NTC | F08 | F16 | F24 | F32 | F40 | S04 | S12 | S20 | S28 | S36 | S44 |

Figure 7B:
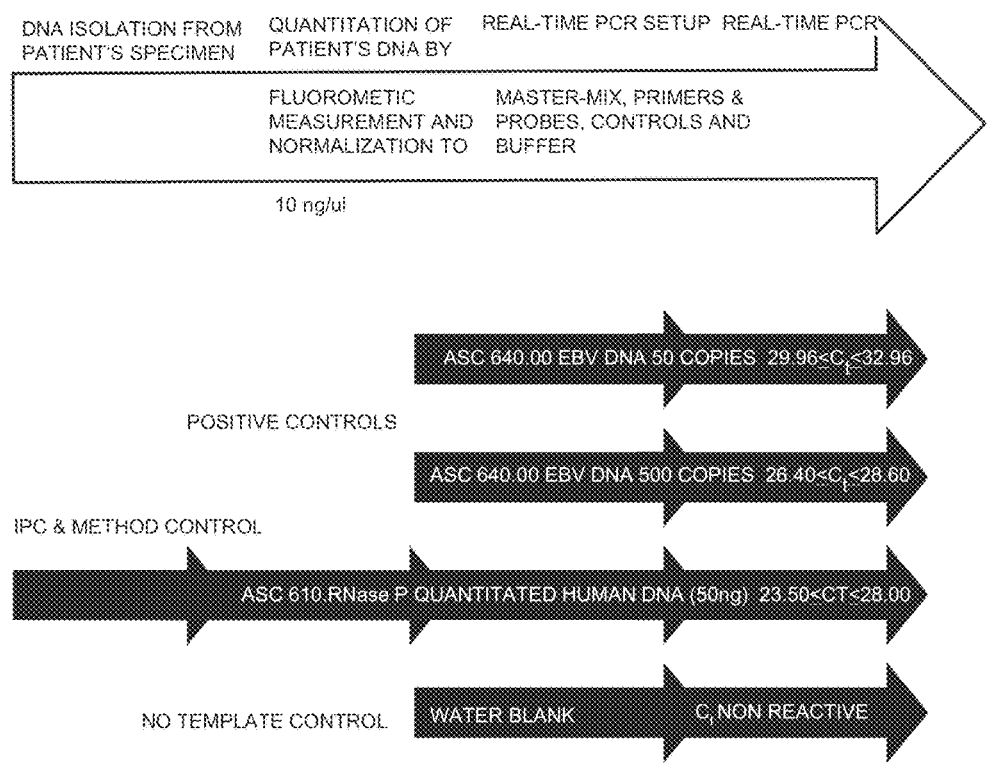
FIG. 7(B) shows the sample flow and controls.

Quality Control:

The assay is intended to provide information about the EBV status in DNA samples isolated from specimen collected from the posterior nasopharynx. This is accomplished by hybridization between the fluorogenic Taqman® probe and EBV genomic target and subsequent production of an identifiable signal which is detected by the ABI PRISM® Sequence Detection System. The analytical sensitivity for the NP Screen® assay is dependent on the combined efficiencies of the hybridization process and the signal detection system. The assay incorporates a series of quantitated controls to verify that the combined elements, which make up the analytical process, behave as expected and within specified upper and lower limits, Table 8 and FIG. 7(B). For each sample tested the assay control results must be within specified limits otherwise the result is not accepted.

concentration and 50 ng (=5 µl×10 ng/µl) are tested. The assay starter template is principally comprised of human DNA (>99.995%) and recovery is evaluated by comparing the raw, real-time PCR output value, Ct(VIC), associated with the detection of the human RNaseP gene to the acceptance standard, $23.00 \leq Ct(VIC) \leq 28.00$, Table 11. Threshold values, Ct(VIC), which fall within the expected reference range verify the method. Frequency: Endogenous with each sample tested.

No Template Controls—(External Water Blank):

The method blank or no template control (NTC) is designed to check for contamination throughout sample processing and PCR analysis. No template controls are introduced during PCR setup using the same sample reagent preparations, sample transfer and PCR procedures as the test samples except sterile molecular grade water replaces DNA

TABLE 8

A summary of the controls used to validate the assay results

| Description | Purpose | Frequency |
|---|---|---|
| Quantitated External Controls (High-Low Control) | Verify PCR master mix and reagents are prepared correctly to amplify the template | 3 @ 50 EBV DNA copies (9.25 fg) and 3 @ 500 EBV DNA copies (92.50 fg) per 96 well plate |
| Quantitated Internal Control (High-Low Control) | Verify interfering substances carried over from extraction process do not inhibit or enhance PCR | RNaseP gene 15,000 copies (3.3 pg) with each patient sample tested |
| Quantitated Internal Method Control (High-Low Control) | Verify the processes from extraction to PCR are working correctly | RNaseP gene 15,000 copies (3.3 pg) with each patient sample tested |
| External PCR Blank (NTC) | Verify that no nucleic acid contaminants have been introduced into the process | 2 @ 5 µl water replicates per 96 well plate |

Quantitated External Control:

The quantitated external controls are used to verify the PCR master mix and reagents were properly prepared to produce amplification of the target DNA sequences and to monitor for EBV contamination. For the assay these controls consist of 3 replicates, 9.25 fg (50 copies), and 3 replicates, 92.50 fg (500 copies), of well characterized EBV DNA reference material, which are run in parallel with but external to patient samples. Recovery is evaluated by comparing the raw real-time PCR output values, Ct(FAM), to an acceptance standard, $26.40 \leq Ct(FAM) \leq 28.60$, for the 92.50 fg quants and $29.96 \leq Ct(FAM) \leq 32.96$ for the 9.25 quants, (Table 10). Frequency: Six per 96 well reaction plate.

Quantitated Internal Control (RNase P):

The quantitated internal control is used to verify that interfering substances, which may have been carried over during DNA isolation and purification process, did not inhibit or enhance PCR. The NP Screen® assay starter template is quantitated (50 ng total DNA) and is principally comprised of human DNA (>99.995%) therefore, an inhibited reaction (or enhanced reaction) may be assessed by comparing the output value, Ct(VIC), associated with the detection of the human RNaseP gene, which exists as single copy per haploid gene, to the acceptance standard, $23.00 \leq Ct(VIC) \leq 28.00$, (Table 11). Threshold values, Ct (VIC)>28.00, may indicate inhibited PCR. Frequency: Endogenous with each sample tested.

Quantitated Method Control (RNase):

The quantitated method control is used to verify that the method performed correctly. Human DNA is method present during all pre analytical and analytical stages of the process. During DNA isolation total DNA is normalized to 10 ng/µl template. NTC results are accepted if non reactive, Table 10. Frequency: Exogenous, two per 96 well reaction plate.

Assay Standardization—Accepted Reference Standard (ARS):

An Accepted Reference Standard (ARS) (True Ct Values) was established for the assay using commercially available Epstein-Barr virus B95.8 Quantitated Viral DNA Control, Catalogue Number 08-926-000 (Advanced Biotechnologies, Inc. MD 21046).

TABLE 9

Accepted Reference Standard for the assay

| EBV DNA Copy Number → | 5 | 50 | 500 | 5,000 | 50,000 |
|---|---|---|---|---|---|
| EBV DNA Mass → | 0.93 fg | 9.25 fg | 92.50 fg | 925.00 fg | 9.25 pg |
| True $C_t$(FAM) Value → | 35.43 | 31.46 | 27.50 | 23.54 | 19.57 |
| Variance Budgets | | | | | |
| % CV → | 2.75% | 2.38% | 2.00% | 1.63% | 1.25% |
| Std Dev $s_v$ → | 0.97 | 0.75 | 0.55 | 0.39 | 0.24 |
| Replicates Tested n → | 84 | 84 | 84 | 21 | 21 |

Plate Specific Controls: Accepting of the Real Time PCR Run:

Two criteria must be met before a real-time PCR run is accepted. The EBV DNA control serves as a quantitated external control to verify the reaction reagents and the instrumentation systems functioned as expected. Three 9.25 fg EBV DNA replicates and three 92.50 fg EBV DNA replicates are run in parallel with the clinical samples. The real-time PCR run is accepted if each of the Ct values for the quantitated external controls is within the upper and lower limits provided in Table 10. Failure of one or both controls may indicate degraded primers or probe, degraded controls, technician errors, system problems or contamination.

Two no template control (NTC) consisting of molecular grade water in place of template verifies no contaminating target nucleic acid(s) was introduced into the reaction during PCR set up. The real-time PCR run is accepted if the NTC Ct results indicate no reaction, Table 10.

TABLE 10

Plate Specific Controls

| Control | Acceptance Range |
| --- | --- |
| All 3 replicates of 9.25 fg EBV DNA Quantitated External Control | $29.96 \leq C_t(FAM) \leq 32.96$ |
| All 3 replicates of 92.50 fg EBV DNA Quantitated External Control | $26.40 \leq C_t(FAM) \leq 28.60$ |
| NTC | Non Reactive |

Sample Specific Controls: Accepting the Individual Test Result:

The dominant DNA isolate in test samples is human DNA (>99.995%). PCR detection and amplification of the human RNase P gene, which exists as a single copy per human genome, serves as the quantitated internal control. The RNase P gene is method present from specimen collection to final PCR and is used to validate the individual test result. Clinical studies determined the True Ct Value for the RNase P target sequences in a 50 ng human DNA test mass corresponded to, Ct(VIC)=25.50±2.50, and the individual test result is accepted if the Ct(VIC) value for the quantitated internal control is within these expected limits.

Higher Ct values may indicate an inhibited or failed reaction, errors in the DNA extraction phase, fluorometric measurement and normalization errors, pipetting errors, compromised reagents or system issues. Lower Ct(VIC) values may indicate fluorometric measurement and normalization errors, pipetting errors, compromised reagents or system issues.

Patient samples are tested in duplicate. Large variation between test duplicates may be caused by pipetting errors or differential heat profiles across the thermocycler heating blocks or other assignable process or equipment errors. Effects from these errors may be limited by monitoring the difference between duplicates. Based on clinical studies the maximum allowable difference between the test duplicates: $\Delta Ct(FAM)<3$ and $\Delta Ct(VIC)<3$.

TABLE 11

Sample Specific Controls

| Analyte Detected | Acceptance Range |
| --- | --- |
| (EBV EBNA-1) Output Value For Patient's 1st Replicate | $19.00 \leq C_t(FAM) \leq 40.00$ |
| (EBV EBNA-1) Output Value For Patient's 2nd Replicate | $19.00 \leq C_t(FAM) \leq 40.00$ |
| (EBV EBNA-1) Difference Between 1st and 2nd Replicates | $\Delta C_t(FAM) \leq 3$ |
| (RNase P) For Patient's 1st Replicate | $23.00 \leq C_t(VIC) \leq 28.00$ |
| (RNase P) For Patient's 2nd Replicate | $23.00 \leq C_t(VIC) \leq 28.00$ |
| (RNase P) Difference Between 1st and 2nd Replicates | $\Delta C_t(VIC) \leq 3$ |

Expected Values:

Patient samples are tested in duplicate and the subordinate Ct(FAM) result is reported. As shown in Table 12, an assay result of 31.50<Ct(FAM)≤40.00 or an EDL<1.7 indicates a low likelihood of EV associated NPC. An assay result of 28.00≤Ct(FAM)≤31.50 or an EDL≥1.7 and EDL≤2.6 is in equivocal result that indicates that the patient may be at a higher than normal risk to develop NPC. An assay result of Ct(FAM)<28.00 or EDL>2.6 indicates a high likelihood of EBV associated NPC.

TABLE 12

Clinical significance of analytical result (Ct(FAM) and EDL)

| Assay Result | Status | Interpretation |
| --- | --- | --- |
| EDL < 1.7<br>31.5 < Ct ≤ 40.00 | Normal | Background incidental cell-free EBV may have been detected due to the ubiquitous nature of EBV. These EBV detection levels are consistent with the normal high- risk population. Low likelihood of EBV associated NPC. Results indicating normal do not preclude future abnormalities. In the absence of other clinical findings the patient is considered normal and should be tested at least annually. Based on clinical trials NP Screen ™ has a Negative Predictive Value = 99.7%. |
| EDL ≥ 1.7<br>and<br>EDL ≤ 2.6<br>28.00 ≤ Ct ≤ 31.50 | Not Normal (Equivocal) | Results in this interval exceed normal background EBV detection levels and may indicate pervasive cell-free EBV or an underlying carcinoma. Persistent, reactivated EBV infections are believed to be antecedent to the development of NPC and this patient may be at a higher than normal risk to develop NPC. A patient with an assay result within this interval must be recalled and retested after 6 to 8 weeks. Patients with assay results, which persist within this interval, should be referred for further clinical investigations or monitored with follow up testing at least semiannually. |
| EDL > 2.6<br>Ct < 28.00 | Not Normal (Abnormal) | Significantly elevated EBV detection levels than that found in the normal high- risk population and is consistent with nasopharyngeal carcinoma. Assay results may be used in conjunction with other clinical presentations to assess a patient's need for a confirmatory procedure. Based on clinical trials NP Screen ™ has a Positive Predictive Value = 96.9%. |

Sensitivity and Specificity:

The clinical performance for the assay at cut-off, Ct=31.50, corresponding to clinical diagnosis is presented in Table 13. The 'Final' clinical status of the patients with 'Initial' false positive results (FP); three patients (3/10) eventually presented clinically (for NPC), six patients (6/10) were negative on retest and thus resolved to normal (TN) and one patient (1/10) on retest maintained his false-positive status without clinical evidence for NPC.

TABLE 13

Initial and Final Assay Performance At Cut-off Ct = 31.50;
Initial and Final Assay Performance At Cut-off Ct = 31.50.

|  | TP | FN | TN | FP | Sensitivity | Specificity |
|---|---|---|---|---|---|---|
| Initial Status | 71 | 1 | 247 | 10 | 98.6% 95% CI [92.4 to 99.8%] | 96.1% 95% CI [93.0 to 97.9%] |
| Final Status | 74 | 1 | 253 | 1 | 98.7% 95% CI [92.8 to 99.8%] | 99.6% 95% CI [97.8 to 99.9%] |

TP = True Positive,
FN = False Negative,
TN = True Negative,
FP = False Positive

TABLE 14

| $C_t$ | EDL | EBV Copies |
|---|---|---|
| 20.00 | 4.59 | 39023 |
| 20.10 | 4.57 | 36821 |
| 20.20 | 4.54 | 34743 |
| 20.30 | 4.52 | 32782 |
| 20.40 | 4.49 | 30932 |
| 20.50 | 4.47 | 29187 |
| 20.60 | 4.44 | 27540 |
| 20.70 | 4.41 | 25986 |
| 20.80 | 4.39 | 24519 |
| 20.90 | 4.36 | 23135 |
| 21.00 | 4.34 | 21830 |
| 21.10 | 4.31 | 20598 |
| 21.20 | 4.29 | 19436 |
| 21.30 | 4.26 | 18339 |
| 21.40 | 4.24 | 17304 |
| 21.50 | 4.21 | 16327 |
| 21.60 | 4.19 | 15406 |
| 21.70 | 4.16 | 14537 |
| 21.80 | 4.14 | 13716 |
| 21.90 | 4.11 | 12942 |
| 22.00 | 4.09 | 12212 |
| 22.10 | 4.06 | 11523 |
| 22.20 | 4.04 | 10872 |
| 22.30 | 4.01 | 10259 |
| 22.40 | 3.99 | 9680 |
| 22.50 | 3.96 | 9134 |
| 22.60 | 3.94 | 8618 |
| 22.70 | 3.91 | 8132 |
| 22.80 | 3.88 | 7673 |
| 22.90 | 3.86 | 7240 |
| 23.00 | 3.83 | 6831 |
| 23.10 | 3.81 | 6446 |
| 23.20 | 3.78 | 6082 |
| 23.30 | 3.76 | 5739 |
| 23.40 | 3.73 | 5415 |
| 23.50 | 3.71 | 5109 |
| 23.60 | 3.68 | 4821 |
| 23.70 | 3.66 | 4549 |
| 23.80 | 3.63 | 4292 |
| 23.90 | 3.61 | 4050 |
| 24.00 | 3.58 | 3822 |
| 24.10 | 3.56 | 3606 |
| 24.20 | 3.53 | 3402 |
| 24.30 | 3.51 | 3210 |

TABLE 14-continued

| $C_t$ | EDL | EBV Copies |
|---|---|---|
| 24.40 | 3.48 | 3029 |
| 24.50 | 3.46 | 2858 |
| 24.60 | 3.43 | 2697 |
| 24.70 | 3.41 | 2545 |
| 24.80 | 3.38 | 2401 |
| 24.90 | 3.36 | 2266 |
| 24.00 | 3.58 | 3822 |
| 24.10 | 3.56 | 3606 |
| 24.20 | 3.53 | 3402 |
| 24.30 | 3.51 | 3210 |
| 24.40 | 3.48 | 3029 |
| 24.50 | 3.46 | 2858 |
| 24.60 | 3.43 | 2697 |
| 24.70 | 3.41 | 2545 |
| 24.80 | 3.38 | 2401 |
| 24.90 | 3.36 | 2266 |
| 25.00 | 3.33 | 2138 |
| 25.10 | 3.30 | 2017 |
| 25.20 | 3.28 | 1903 |
| 25.30 | 3.25 | 1796 |
| 25.40 | 3.23 | 1695 |
| 25.50 | 3.20 | 1599 |
| 25.60 | 3.18 | 1509 |
| 25.70 | 3.15 | 1424 |
| 25.80 | 3.13 | 1343 |
| 25.90 | 3.10 | 1267 |
| 26.00 | 3.08 | 1196 |
| 26.10 | 3.05 | 1128 |
| 26.20 | 3.03 | 1065 |
| 26.30 | 3.00 | 1005 |
| 26.40 | 2.98 | 948 |
| 26.50 | 2.95 | 894 |
| 26.60 | 2.93 | 844 |
| 26.70 | 2.90 | 796 |
| 26.80 | 2.88 | 751 |
| 26.90 | 2.85 | 709 |
| 27.00 | 2.83 | 669 |
| 27.10 | 2.80 | 631 |
| 27.20 | 2.77 | 596 |
| 27.30 | 2.75 | 562 |
| 27.40 | 2.72 | 530 |
| 27.50 | 2.70 | 500 |
| 27.60 | 2.67 | 472 |
| 27.70 | 2.65 | 445 |
| 27.80 | 2.62 | 420 |
| 27.90 | 2.60 | 397 |
| 28.00 | 2.57 | 374 |
| 28.10 | 2.55 | 353 |
| 28.20 | 2.52 | 333 |
| 28.30 | 2.50 | 314 |
| 28.40 | 2.47 | 297 |
| 28.50 | 2.45 | 280 |
| 28.60 | 2.42 | 264 |
| 28.70 | 2.40 | 249 |
| 28.80 | 2.37 | 235 |
| 28.90 | 2.35 | 222 |
| 29.00 | 2.32 | 209 |
| 29.10 | 2.30 | 198 |
| 29.20 | 2.27 | 186 |
| 29.30 | 2.25 | 176 |
| 29.40 | 2.22 | 166 |
| 29.50 | 2.19 | 157 |
| 29.60 | 2.17 | 148 |
| 29.70 | 2.14 | 139 |
| 29.80 | 2.12 | 132 |
| 29.90 | 2.09 | 124 |
| 30.00 | 2.07 | 117 |
| 30.10 | 2.04 | 111 |
| 30.20 | 2.02 | 104 |
| 30.30 | 1.99 | 98 |
| 30.40 | 1.97 | 93 |
| 30.50 | 1.94 | 88 |
| 30.60 | 1.92 | 83 |
| 30.70 | 1.89 | 78 |
| 30.80 | 1.87 | 74 |
| 30.90 | 1.84 | 69 |
| 31.00 | 1.82 | 66 |

TABLE 14-continued

| $C_t$ | EDL | EBV Copies |
|---|---|---|
| 31.10 | 1.79 | 62 |
| 31.20 | 1.77 | 58 |
| 31.30 | 1.74 | 55 |
| 31.40 | 1.72 | 52 |
| 31.50 | 1.69 | 49 |
| 31.60 | 1.66 | 46 |
| 31.70 | 1.64 | 44 |
| 31.80 | 1.61 | 41 |
| 31.90 | 1.59 | 39 |
| 32.00 | 1.56 | 37 |
| 32.10 | 1.54 | 35 |
| 32.20 | 1.51 | 33 |
| 32.30 | 1.49 | 31 |
| 32.40 | 1.46 | 29 |
| 32.50 | 1.44 | 27 |
| 32.60 | 1.41 | 26 |
| 32.70 | 1.39 | 24 |
| 32.80 | 1.36 | 23 |
| 32.90 | 1.34 | 22 |
| 33.00 | 1.31 | 21 |
| 33.10 | 1.29 | 19 |
| 33.20 | 1.26 | 18 |
| 33.30 | 1.24 | 17 |
| 33.40 | 1.21 | 16 |
| 33.50 | 1.19 | 15 |
| 33.60 | 1.16 | 14 |
| 33.70 | 1.14 | 14 |
| 33.80 | 1.11 | 13 |
| 33.90 | 1.08 | 12 |
| 34.00 | 1.06 | 11 |
| 34.10 | 1.03 | 10.8 |
| 34.20 | 1.01 | 10.2 |
| 34.30 | 0.98 | 9.6 |
| 34.40 | 0.96 | 9.1 |
| 34.50 | 0.93 | 8.6 |
| 34.60 | 0.91 | 8.1 |
| 34.70 | 0.88 | 7.6 |
| 34.80 | 0.86 | 7.2 |
| 34.90 | 0.83 | 6.8 |
| 35.00 | 0.81 | 6.4 |
| 35.10 | 0.78 | 6.1 |
| 35.20 | 0.76 | 5.7 |
| 35.30 | 0.73 | 5.4 |
| 35.40 | 0.71 | 5.1 |
| 35.50 | 0.68 | 4.8 |
| 35.60 | 0.66 | 4.5 |
| 35.70 | 0.63 | 4.3 |
| 35.80 | 0.61 | 4.0 |
| 35.90 | 0.58 | 3.8 |
| 36.00 | 0.55 | 3.6 |
| 36.10 | 0.53 | 3.4 |
| 36.20 | 0.50 | 3.2 |
| 36.30 | 0.48 | 3.0 |
| 36.40 | 0.45 | 2.8 |
| 36.50 | 0.43 | 2.7 |
| 36.60 | 0.40 | 2.5 |
| 36.70 | 0.38 | 2.4 |
| 36.80 | 0.35 | 2.3 |
| 36.90 | 0.33 | 2.1 |
| 37.00 | 0.30 | 2.0 |
| 37.10 | 0.28 | 1.9 |
| 37.20 | 0.25 | 1.8 |
| 37.30 | 0.23 | 1.7 |
| 37.40 | 0.20 | 1.6 |
| 37.50 | 0.18 | 1.5 |
| 37.60 | 0.15 | 1.4 |
| 37.70 | 0.13 | 1.3 |
| 37.80 | 0.10 | 1.3 |
| 37.90 | 0.08 | 1.2 |
| 38.00 | 0.05 | 1.1 |
| 38.10 | 0.03 | 1.1 |
| 38.20 | 0.00 | 1.0 |

TABLE 15

Table of Sequences

SEQ ID NO: 1:
5'-GTC GTC TCC CCT TTG GAA TG-3'

SEQ ID NO: 2:
5'-AAT AAC AGA CAA TGG ACT CCC TTA GC-3'

SEQ ID NO: 3:
GTCGTCTCCCCTTTGGAATGGCCCCTGGACCCGGCCCACAACCTGGC
CCGCTAAGGAGTCCATTGTCTGTTATT

SEQ ID NO: 4:
5'-CCT GGA CCC GGC CCA CAA CC-3'

REFERENCES

1. Ung A, Chen C J, Levine P H, et al. Familial and sporadic cases of nasopharyngeal carcinoma in Taiwan. Anticancer Res 1999; 19:661-665.
2. Pathmanathan R, Prasad U, Sadler R, Flynn K, Raab-Traub N. Clonal proliferations of cells infected with Epstein-Barr virus in preinvasive lesions related to nasopharyngeal carcinoma. N Engl J Med 1995; 333:693-698.
3. Skinner D W, Van H C. Nasopharyngeal carcinoma: methods of presentation. Ear Nose Throat J 1990; 69:237-240.
4. Ho S, Teo P, Kwan W H, Choi P, Tjong J, Johnson P J. Staging and IgA VCA titre in patients with nasopharyngeal carcinoma: changes over a 12-year period. Oral Oncol 1998; 34:491-495.
5. Liu M T, Yeh C Y. Prognostic value of anti-Epstein-Barr virus antibodies in nasopharyngeal carcinoma (NPC). Radiat Med 1998; 16:113-117.
6. Zeng Y, Pi G H, Deng H, et al. Epstein-Barr virus seroepidemiology in China. AIDS Res 1986; 2 Suppl1: S7-15.
7. Feinmesser R, Miyazaki I, Cheung R, Freeman J L, Noyek A M, Dosch H-M. Diagnosis of nasopharyngeal carcinoma by DNA amplification of tissue obtained by fine-needle aspiration. N Engl J Med 1992; 326:17-21.
8. Tune C E, Liavaag P G, Freeman J L, et al. Nasopharyngeal brush biopsies and detection of nasopharyngeal cancer in a high-risk population. J Natl Cancer Inst 1999; 91:796-80.
9. Shi M M. Enabling large-scale pharmacogenetic studies by high-throughput mutation detection and genotyping technologies. Clin Chem 2001; 47:164-172.
10. Hardin J A, Sherr D H, DeMaria M, Lopez P A. A simple fluorescence method for surface antigen phenotyping of lymphocytes undergoing DNA fragmentation. J Immunol Methods 1992; 154:99-107.
11. Zweig M H, Campbell G. Receiver-operating characteristic (ROC) plots: a fundamental evaluation tool in clinical medicine. Clin Chem 1993; 39:561-577.
12. Low W K, Leong J L, Goh Y H, Fong K W. Diagnostic value of Epstein-Barr viral serology in nasopharyngeal carcinoma. Otolaryngol Head Neck Surg 2000; 123:505-507.
13. Low W K, Leong J L. Correlating clinical appearance of nasopharyngeal carcinoma with tumor staging. J Roy Coil Surg Edinb 2000; 45:146-148.
14. Sham J S T, Wei W I, Kwan W H, Chan C W, Choi P H K, Choy D. Fiberoptic endoscopic examination and biopsy in determining the extent of nasopharyngeal carcinoma. Cancer 1989; 64:1838-1842.
15. Raab-Traub N, Flynn K, Pearson G, Huang A, Levine P, Lanier A, Pagano J. The differentiated form of nasopharyngeal carcinoma contains Epstein-Barr virus DNA. Int J Cancer. 1987 Jan. 15; 39(1):25-9.
16. Wei W I, Sham J S. Nasopharyngeal Carcinoma. Lancet. 2005; 365:2041-2054.
17. Ferlay J, Shin H R, Bray F, et al. Estimates of worldwide burden of cancer in 2008: GLOBOCAN 2008. Int J Cancer. 2010; 127(12):2893-2917.
18. Jia W H, Huang Q H, Liao J, et al. Trends in incidence and mortality of nasopharyngeal carcinoma over a 20-25 year period (1978/1983-2002) in Sihui and Cangwu counties in southern China. BMC Cancer. 2006; 6:178
19. Cao S M, Simons M J, Qian C N. The prevalence and prevention of nasopharyngeal carcinoma in China. Chin J Cancer. 2011; 30(2):114-119.
20. Lo Y M D, Chan L Y, Chan A T, et al. Quantitative and temporal correlation between circulating cell-free Epstein-Barr virus DNA and tumor recurrence in nasopharyngeal carcinoma. Cancer Res. 1999a; 59:5452-5455.
21. Lo Y M D, Chan L Y S, Lo K W, et al. Quantitative analysis of cell-free Epstein-Barr virus DNA in plasma of patients with nasopharyngeal carcinoma. Cancer Res. 1999b; 59:1188-1199.
22. Lo Y M D, Leung S, Chan L Y, et al. Kinetics of plasma Epstein-Barr virus DNA during radiation therapy for nasopharyngeal carcinoma. Cancer Res. 2000; 60:2351-2355.
23. Tune C E, Liavaag P G, Freeman J L, et al. Nasopharyngeal brush biopsies and detection of nasopharyngeal cancer in a high-risk population. J Natl Cancer Inst. 1999; 91:796-880.
24. Teresa M., Yu G, Hu K., Li J. Plasma Epstein-Barr Virus Immunoglobulin A and DNA for nasopharyngeal carcinoma screening in the United States. Otolaryngology-Head and Neck Surgery. 2007; 136:992-997.
25. Tsang R K, Vlantis A C, Ho R W, Tam J S, To K F, Van Hasselt C A. Sensitivity and specificity of Epstein-Barr virus IGA titer in the diagnosis of nasopharyngeal carcinoma: a three-year institutional review. Head Neck. 2004; 26(7):598-602.
26. Cheng W M, Chan K H, Chen H L, Luo R X, Ng S P, Luk W, Zheng B J, Ji M F, Liang J S, Sham J S T, Wang D K, Zong Y S, Ng M H. Assessing the risk of nasopharyngeal carcinoma on the basis of EBV antibody spectrum. Int J Cancer. 2002; 97(4):489-492.
27. Stevens S J, Verkuijlen S A, Hariwiyanto B, Harijadi, Fachiroh J, Paramita D K, et al. Diagnostic value of measuring Epstein-Barr virus (EBV) DNA load and carcinoma-specific viral mRNA in relation to anti-EBV immunoglobulin A (IgA) and IgG antibody levels in blood of nasopharyngeal carcinoma patients from Indonesia. J Clin Microbiol. 2005; 43:3066-3073.
28. Le Q T, Jones C D, Yau T K, Shirazi H A, Wong P H, Thomas E N, et al. A Comparison study of different PCR assays in measuring circulating Plasma Epstein-Barr virus DNA levels in patients with nasopharyngeal carcinoma. Clin Cancer Res. 2005; 11:5700-5707.
29. Anker P, Mulcahy H, Chen X Q, Stroun M. Detection of circulating tumour DNA in the blood (plasma/serum) of cancer patients. Cancer Metastasis Rev. 1999; 18:65-73.
30. Leung S F, Tam J S, Chan A T C, et al. Improved accuracy of detection of nasopharyngeal carcinoma by combined application of circulating Epstein-Barr virus DNA and anti-Epstein-Barr viral capsid antigen IgA antibody. Clin Chem. 2004; 50:339-345.
31. Adham M, Greijer A E, Verkuijlen S A, Juwana H, Fleig S, Rachmadi L, Malik O, Kurniawan A N, Roezin A, Gondhowiardjo S, Atmakusumah D, Stevens S J, Hermani B, Tan I B, Middeldorp J M. Epstein-Barr Virus DNA Load in Nasopharyngeal Brushings and Whole Blood in Nasopharyngeal Carcinoma Patients before and after Treatment. Clin Cancer Res. 2013; 19(8); 2175-2186.
32. Mutirangura A, Pornthanakasaem W, Theamboonlers A, et al. Epstein-Barr viral DNA in serum of patients with nasopharyngeal carcinoma. Clin Cancer Res. 1998; 4:665-669.
33. Fournie G J, Courtin J P, Laval F, et al. Plasma DNA as a marker of cancerous cell death. Investigations in patients suffering from lung cancer and in nude mice bearing human tumors. Cancer Lett. 1995; 91:221-227.
34. Tong J, Ka-Fai To, et al. Quantitative Epstein-Barr Virus DNA Analysis and Detection of Gene Parameter Hypermethylation in Nasopharyngeal Brushing Samples from Patients with N P Carcinoma. Clinical Cancer Research. 2002; 8:2612
35. Low W K, Leong J L. Correlating clinical appearance of nasopharyngeal carcinoma with tumor staging. J R Coil Surg Edinb. 2000; 45(3):146-147.
36. Sham J S T, Wei W I, Kwan W H, et al. Fiberoptic endoscopic examination and biopsy in determining the extent of nasopharyngeal carcinoma. Cancer. 1989; 64:1838-1842.
37. Liu Y, Fang A, Liu L, Yang S, Zhang L. Detection of Epstein-Barr Virus DNA in serum or plasma for nasopharyngeal cancer: a meta analysis. Genet Test Mol biomarkers. 2011; 15(7-8):495-502.
38. Liu Y, Huang Q, Liu W, Liu Q, Jia W, Chang E, Chen F, Liu Z, Guo X, Mo H, Chen J, Rao D, Ye W, Cao S, Hong M. Establishment of VCA and EBNA1 IgA-based combination by enzyme-linked immunosorbent assay as preferred screening method for nasopharyngeal carcinoma: a two-stage design with a preliminary performance study and a mass screening in southern China. Int. J. Cancer. 2012; 131(2):406-416.
39. Yang X, Goldstein A M, Chen C J, Rabkin C S, Chen J Y, Cheng Y J, et al. Distribution of Epstein-Barr viral load in serum of individuals from nasopharyngeal carcinoma high-risk families in Taiwan. Int J Cancer. 2006; 118:780-784.
40. Bortolin M T, Pratesi C, Dolcetti R, Bidoli E, Vaccher E, Zanussi S, et al. Clinical value of Epstein-Barr Virus DNA levels in peripheral blood samples of Italian patients with undifferentiated carcinoma of nasopharyngeal type. Cancer Lett. 2006; 233:247-254.
41. Lin J C, Wang W Y, Chen K Y, Wei Y H, Liang W M, Jan J S, et al. Quantification of plasma Epstein-Barr Virus DNA in patients with advanced nasopharyngeal carcinoma. N Engl J Med. 2004; 350:2461-2470.
42. Maeda E, Akahane M, Kiryu S, Kato N, Yoshikawa T, Hayashi N, Aoki S, Minami M, Uozaki H, Fukayama M, Ohtomo K. Spectrum of Epstein-Barr virus-related diseases: a pictorial review. Jpn J Radiol. 2009; 27(1):4-19.
43. Savard M, Belanger C, Tardif M, Gourde P, Flamand L, Gosselin J. Infection of primary human monocytes by Epstein-Barr virus. J. Virol. 2000; 74(6):2612-2619.
44. Gulley M L, Tang W. Laboratory assays for Epstein-Barr virus related disease. J Mol Diagn. 2008; 10(4):279-292.
45. Lo Y M, Chan A T, Chan L Y, Leung S F, Lam C W, Huang D P, Johnson P J. Molecular prognostication of nasopharyngeal carcinoma by quantitative analysis of circulating Epstein-Barr virus DNA. Cancer Res. 2000; 60(24):6878-6881.
46. Chan A T, Lo Y M, Zee B, Chan L Y, Ma B B, Leung S F, et al. Plasma Epstein-Barr virus DNA and residual disease after radiotherapy for undifferentiated nasopharyngeal carcinoma. J Natl Cancer Inst. 2002; 94:1614-1619.
47. Leon S A, Shapiro B, Sklaroff D M, Yaros M J. Free DNA in the serum of cancer patients and the effect of therapy. Cancer Res. 1977; 37:646-650.
48. Usadel H, Brabender J, Danenberg K D, Jeronimo C, Harden S, Engles J, et al. Quantitative adenomatous polyposis coli promoter methylation analysis in tumor tissue, serum, and plasma DNA of patients with lung cancer. Cancer Res. 2002; 62:371-375.
49. Shao Z M, Wu J, Shen Z Z, Nguyen M. P53 mutation in plasma DNA and its prognostic value in breast cancer patients. Clin Cancer Res. 2001; 7:2222-2227.
50. Anker P, Mulcahy H, Stroun M. Circulating nucleic acids in plasma and serum as a noninvasive investigation for cancer: time for large-scale clinical studies?. Int J Cancer. 2003; 103:149-152.
51. Macsween K F, Crawford D H. Epstein-Barr Virus: Recent Advances. Lancet Infect Dis 2003; 3:131-40

What is claimed is:

1. A method of detecting nasopharyngeal carcinoma or a risk of developing nasopharyngeal carcinoma in a test subject comprising:
   a. providing a nasopharyngeal sample obtained transorally from the fossae of Rosenmueller of the subject using a brush biopsy,
   b. isolating DNA from the sample,
   c. amplifying and detecting at least one EBV target sequence from the DNA using real-time PCR, wherein a real-time PCR cycle threshold number is verified based on batch specific, plate specific, sample specific, and quantitated EBV DNA controls, and
wherein a real-time PCR cycle threshold number of less than or equal to 31.5 is indicative of the test subject having nasopharyngeal carcinoma or a risk of developing nasopharyngeal carcinoma.

2. The method of claim 1, wherein a real-time PCR cycle threshold number of 28 to 31.5 is indicative of the test subject having a risk of developing nasopharyngeal carcinoma.

3. The method of claim 1, wherein a real-time PCR cycle threshold number of less than 28 is indicative of the test subject having nasopharyngeal carcinoma.

4. The method of claim 1 further comprising determining an Epstein-Barr Virus Detection Level (EDL) based on the real-time PCR cycle threshold number, wherein an EDL of greater than or equal to 2.57 is indicative of the test subject having nasopharyngeal carcinoma.

5. The method of claim 1, wherein the nasopharyngeal sample comprises epithelial cells.

6. The method of claim 1, wherein the at least one EBV target sequence is amplified from 40-60 ng, optionally about 50 ng of DNA.

7. The method of claim 1, wherein the at least one EBV target sequence is in the EBNA1 gene.

8. The method of claim 1, wherein the at least one EBV target sequence is amplified using primers corresponding to SEQ ID NO: 1 and 2.

9. The method of claim 6, wherein the at least one EBV target sequence is detected using a probe corresponding to SEQ ID NO: 4, wherein the probe is labeled with a reporter fluorophore at the 5'-end and a quencher fluorophore at the 3'-end.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gtcgtctccc ctttggaatg                                                 20

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aataacagac aatggactcc cttagc                                          26

<210> SEQ ID NO 3
<211> LENGTH: 74
<212> TYPE: DNA
<213> ORGANISM: Epstein-Barr Virus

<400> SEQUENCE: 3
gtcgtctccc ctttggaatg gcccctggac ccggcccaca acctggcccg ctaaggagtc     60
cattgtctgt tatt                                                       74

<210> SEQ ID NO 4
<211> LENGTH: 20
<212> TYPE: DNA
<213> ORGANISM: Artificial Sequence
<220> FEATURE:
<223> OTHER INFORMATION: Probe

<400> SEQUENCE: 4
cctggacccg gcccacaacc                                                 20
```